United States Patent [19]

Sprecker et al.

[11] Patent Number: 4,615,830
[45] Date of Patent: * Oct. 7, 1986

[54] ISOMER-DIRECTED PROCESS FOR PRODUCING ASYMMETRIC KETONES USING CATALYTIC CLAISEN REARRANGEMENT OF ALLYLIC ETHERS, INTERMEDIATES, AND USES OF PRODUCTS AND INTERMEDIATES OF PROCESS IN PERFUMERY

[75] Inventors: Mark A. Sprecker, Sea Bright; Robert P. Belko, Woodbridge; William L. Schreiber, Jackson; Michael Licciardello, Little Silver, all of N.J.

[73] Assignee: International Flavors & Fragrances Inc., New York, N.Y.

[ * ] Notice: The portion of the term of this patent subsequent to Mar. 18, 2003 has been disclaimed.

[21] Appl. No.: 765,278

[22] Filed: Aug. 13, 1985

Related U.S. Application Data

[62] Division of Ser. No. 602,646, Apr. 20, 1984, Pat. No. 4,548,743.

[51] Int. Cl.$^4$ ............................................. A61K 7/46
[52] U.S. Cl. ................................ 252/522 R; 568/376; 568/377; 568/361; 568/591
[58] Field of Search ............... 568/591, 361, 376, 377; 252/522 R

[56] References Cited

U.S. PATENT DOCUMENTS

| | | | |
|---|---|---|---|
| 4,424,379 | 1/1984 | Sprecker et al. | 252/522 R |
| 4,465,863 | 8/1984 | Boden | 252/522 R |
| 4,481,372 | 11/1984 | Boden et al. | 568/378 |
| 4,504,398 | 3/1985 | Evans et al. | 252/522 R |

OTHER PUBLICATIONS

Denmark et al, J.A.C.S., vol. 104, p. 4972 (1982).
Daub et al, Tet. Letters, vol. 24(41), pp. 4397–4400 (1983).
Hurd et al, J.A.C.S., vol. 60, p. 1908 (1938).

*Primary Examiner*—James H. Reamer

*Attorney, Agent, or Firm*—Arthur L. Liberman

[57] ABSTRACT

Described is an isomer-directed process for producing asymmetric ketones defined according to the generic structure:

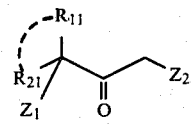

wherein one of $Z_1$ or $Z_2$ is the moiety:

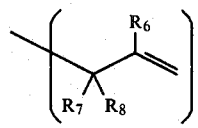

and the other of $Z_1$ or $Z_2$ is hydrogen; wherein $R_{11}$ and $R_{21}$ represent hydrogen or the same or different alkyl or alkenyl with the proviso that $R_{11}$ and $R_{21}$ are not both hydrogen or wherein $R_{11}$ and $R_{21}$ taken together:
  (i) complete a cycloalkyl, cycloalkenyl, bicycloalkyl, mono or polyalkyl cycloalkyl or mono or polyalkyl cycloalkenyl ring, or
  (ii) represent alkylidene, cycloalkenyl alkylidene, aralkylidene, mono or polyalkyl cycloalkenyl alkylidene or mono or polyalkyl aralkylidene;

and wherein $R_6$, $R_7$ and $R_8$ are the same or different and each represents hydrogen or methyl, using a catalytic Claisen rearrangement of allylic ethers previously formed by reacting substituted or unsubstituted allylic alcohols defined according to the structure:

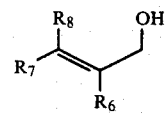

with dialkyl ketals defined according to the structure:

(Abstract continued on next page.)

4,615,830
Page 2
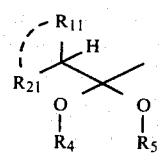
wherein $R_4$ and $R_5$ represent the same or different $C_1$–$C_4$ alkyl.
Also described are compounds and processes for using same in perfumery defined according the structures:
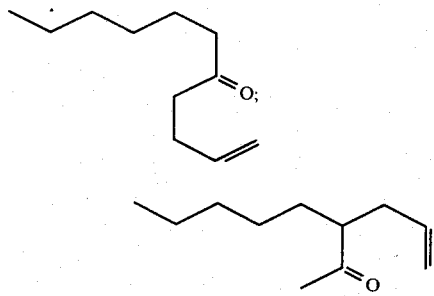
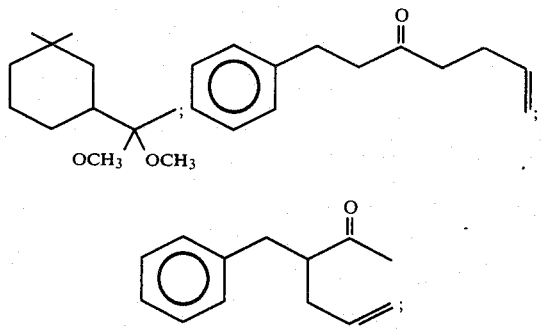
-continued
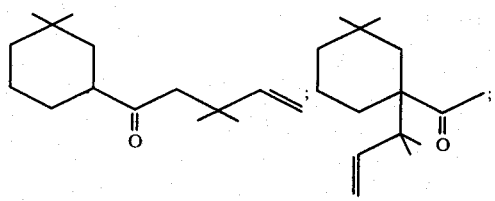
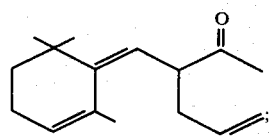
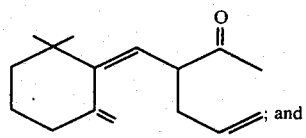
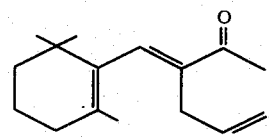
Also described are certain diallylic ethers defined according to the generic structure:
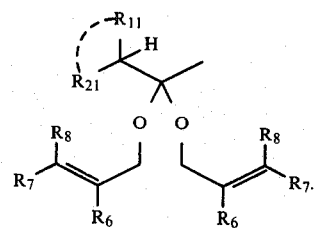
4 Claims, 18 Drawing Figures

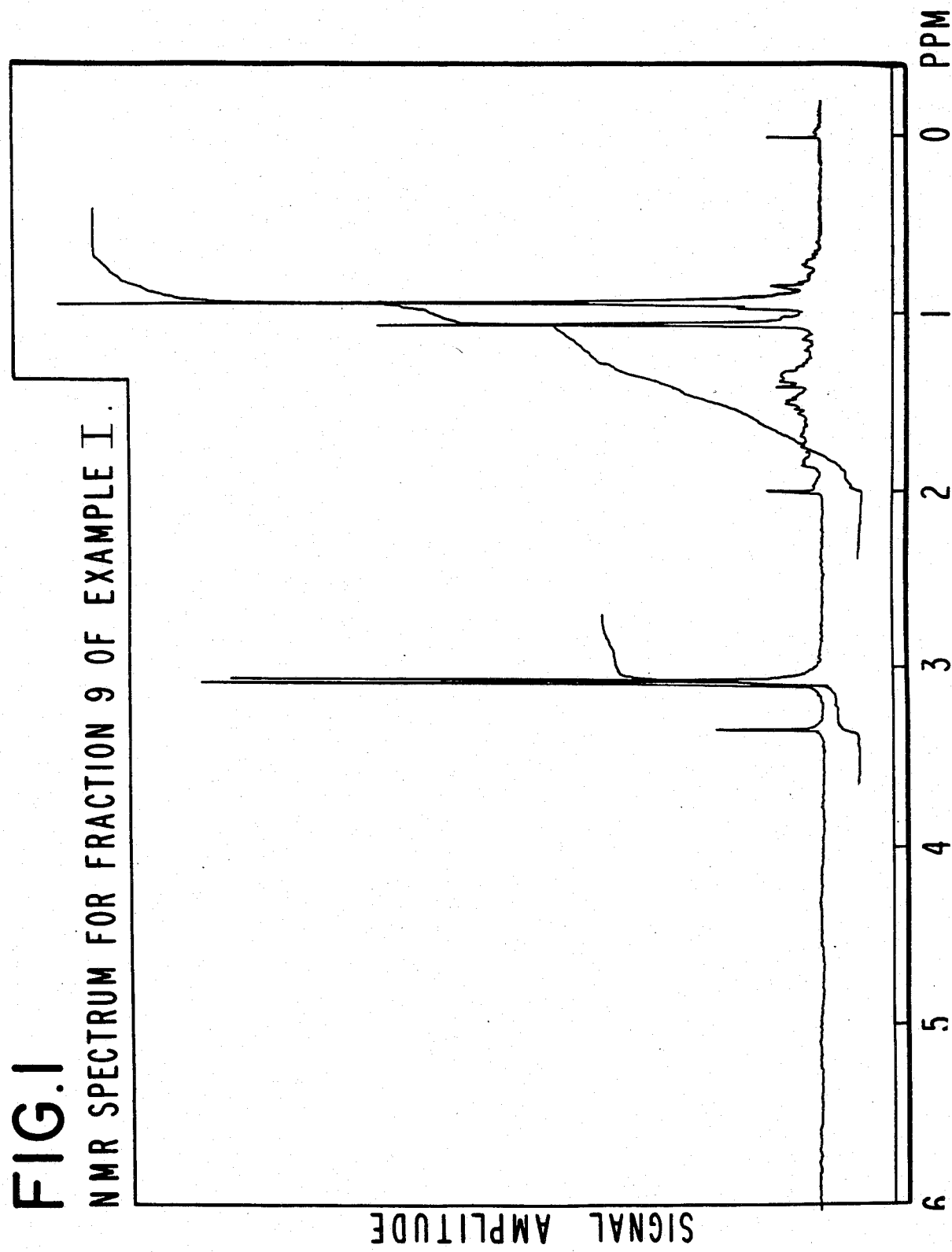
FIG.1 NMR SPECTRUM FOR FRACTION 9 OF EXAMPLE I.

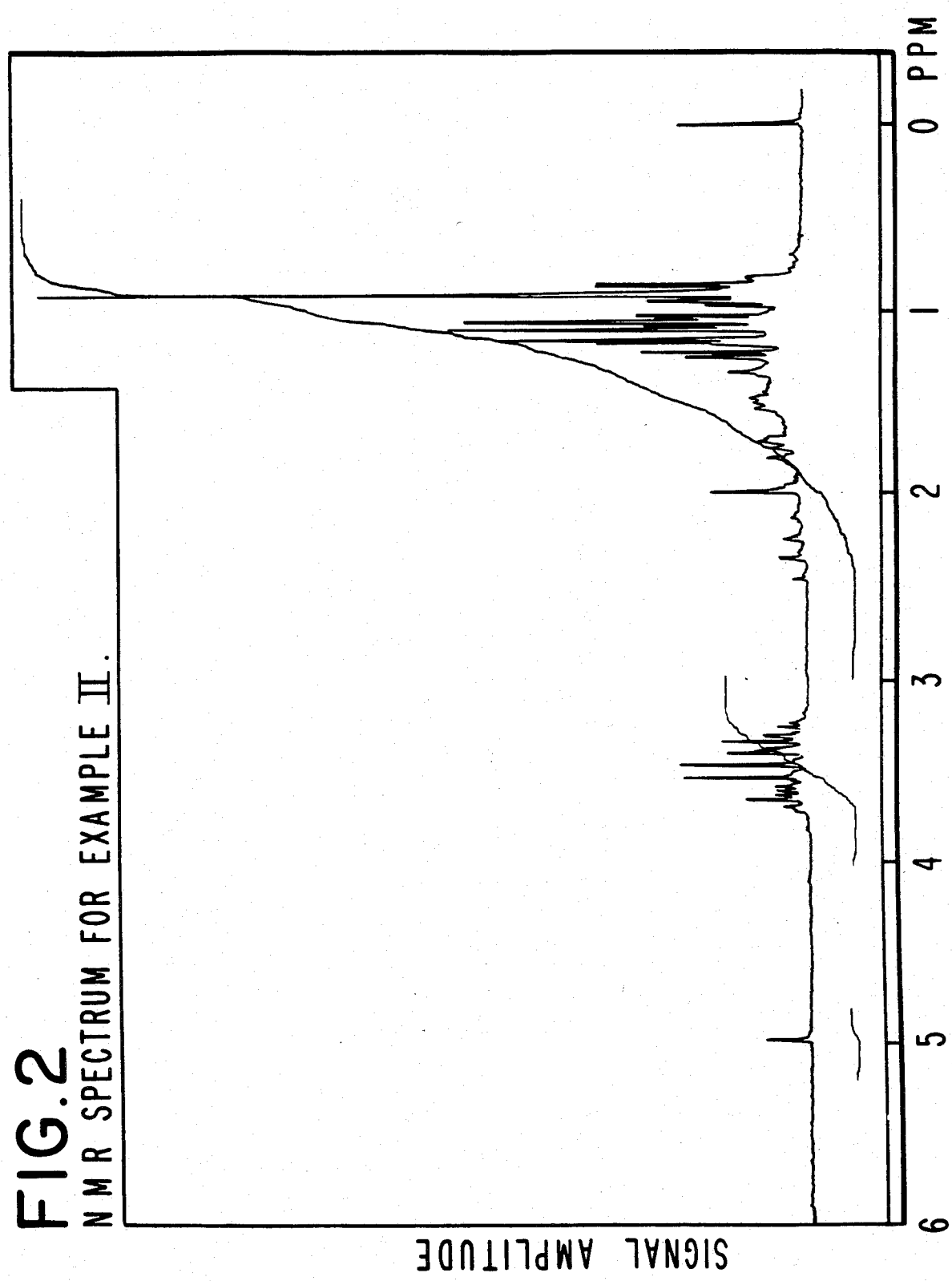
FIG. 2 NMR SPECTRUM FOR EXAMPLE II.

GLC PROFILE FOR EXAMPLE V.

GLC PROFILE FOR EXAMPLE IV.

CRUDE

GLC PROFILE FOR EXAMPLE VII.

GLC PROFILE FOR EXAMPLE VI(c).
CRUDE

GLC PROFILE FOR EXAMPLE VIII CRUDE

GLC PROFILE FOR FRACTION 6 OF EXAMPLE VII.

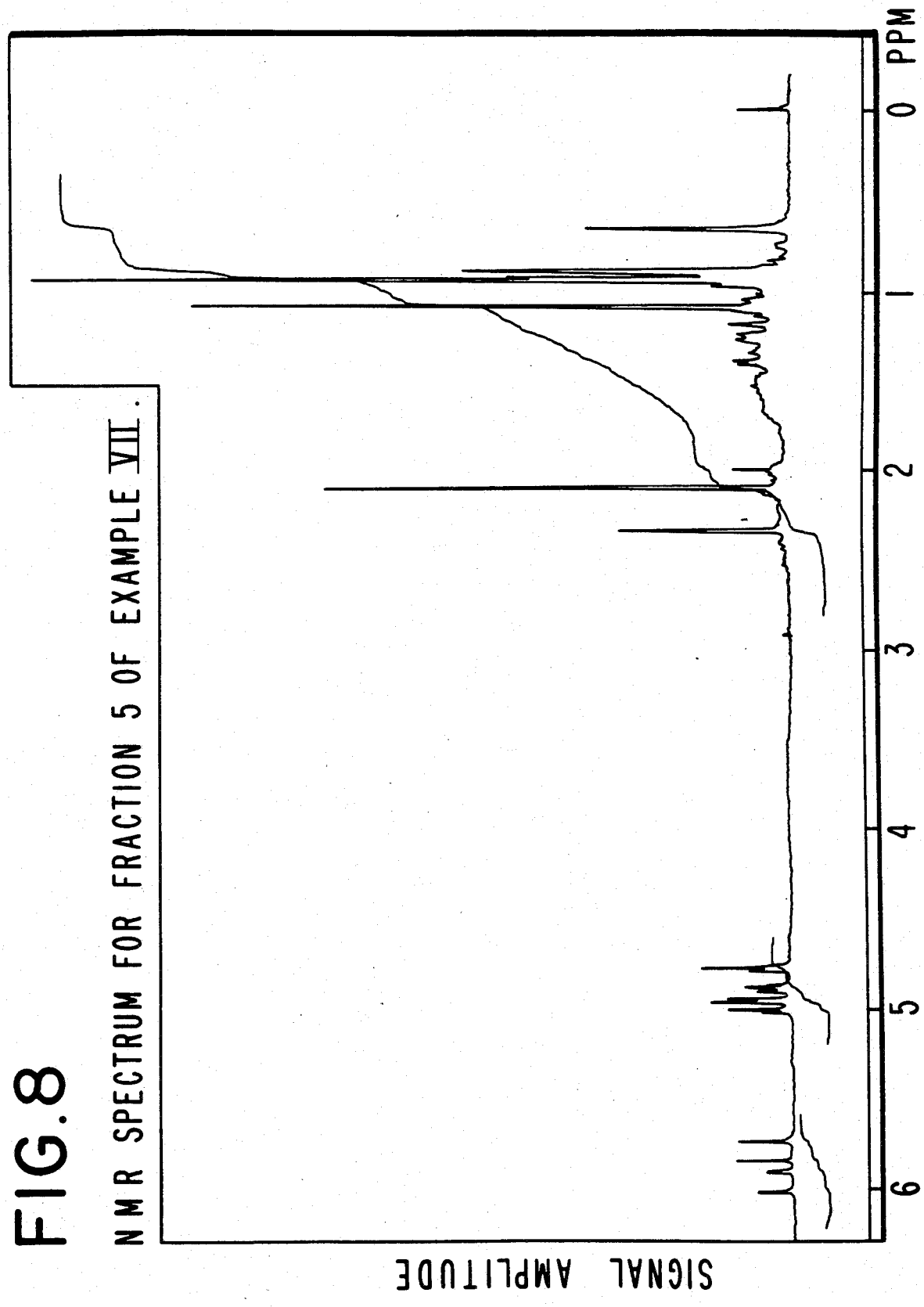
FIG. 8 NMR SPECTRUM FOR FRACTION 5 OF EXAMPLE VII.

IR SPECTRUM FOR EXAMPLE VIII.

NMR SPECTRUM FOR FRACTION 1ª OF EXAMPLE VIII.

NMR SPECTRUM FRACTION 8 OF EXAMPLE VIII.

GLC PROFILE FOR EXAMPLE IX.

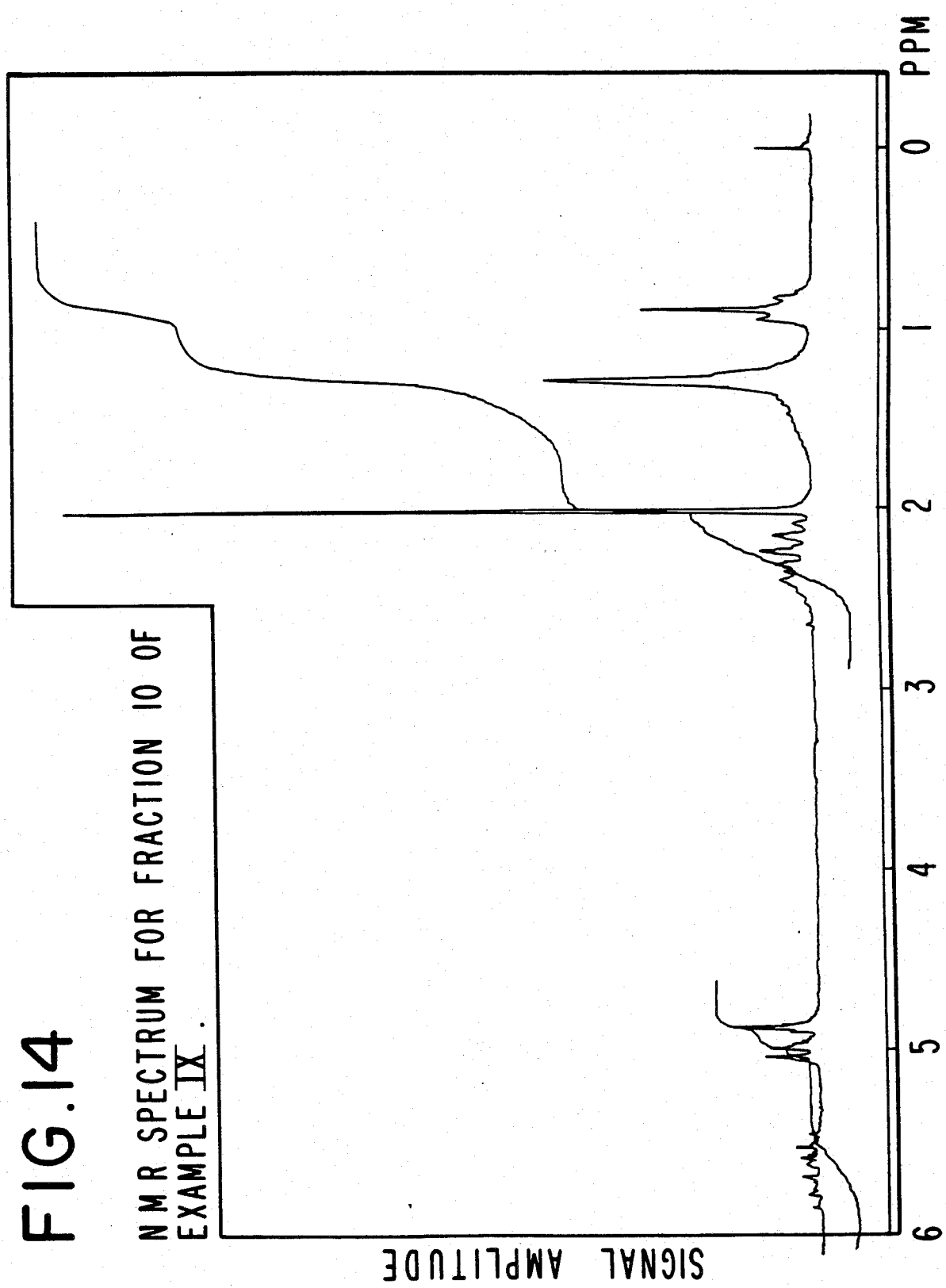
FIG. 14 NMR SPECTRUM FOR FRACTION 10 OF EXAMPLE IX.

GLC PROFILE FOR BULKED FRACTIONS 7 TO 15. 2ND DISTILLATION OF EXAMPLE X.

GLC PROFILE FOR EXAMPLE X. CRUDE

GLC PROFILE FOR EXAMPLE X(B)
FRACTION 14.
SECOND DISTILLATION

GLC PROFILE FOR EXAMPLE X(B).
CRUDE

ISOMER-DIRECTED PROCESS FOR PRODUCING ASYMMETRIC KETONES USING CATALYTIC CLAISEN REARRANGEMENT OF ALLYLIC ETHERS, INTERMEDIATES, AND USES OF PRODUCTS AND INTERMEDIATES OF PROCESS IN PERFUMERY

This is a divisional of application Ser. No. 602,646, filed 4/20/84 now U.S. Letters Pat. No. 4,548,743 issued on Oct. 22, 1985.

BACKGROUND OF THE INVENTION

U.S. Pat. Nos. 4,064,281 issued Dec. 20, 1977 and 4,102,928 issued July 25, 1978 describe processes for preparing compounds defined according to the structure:

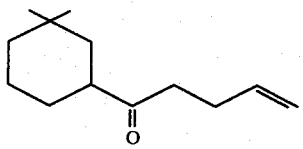

in low yields by reaction of an allylic halide with acetyl-3,3-dimethylcyclohexane in the presence of a phase transfer catalyst. Primarily U.S. Pat. No. 4,064,281 teaches the reaction:

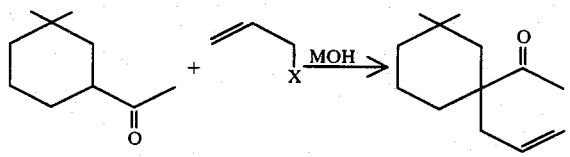

(wherein X is chloro or bromo and M is alkali metal). The compound having the structure:

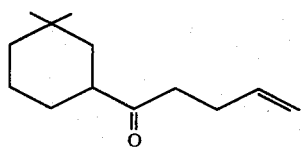

is prepared incidentally to that reaction. Dutch Published application No. 7500838 discloses the preparation of the compound having the structure:

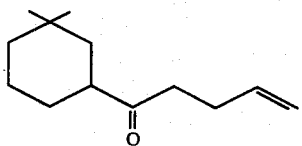

in a manner different in kind from the instant process giving rise to yields far below the yields produced according to the instant process and discloses its use in perfumery and in augmenting foodstuff flavors. The perfumery use of this compound and other members of its class is described as "floral, green, herbaceous and chypre". The use as a galbanum component is also disclosed therein.

Furthermore, allyl alpha and beta ionones are known for their uses in augmenting or enhancing the organoleptic properties of consumable materials such as foodstuffs, chewing gums, medicinal products, perfumes, perfume compositions, colognes and perfumed articles. Thus, Arctander "Perfume and Flavor Chemicals (Aroma Chemicals)", Volume I, 1969, at Monograph 86 indicates that allyl ionone ("alpha allyl ionone") having the structure:

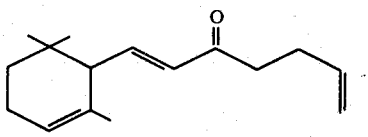

has an oily-sweet, slightly flowery but also fruity, woody and bark-like, green odor of considerable tenacity. Arctander further states that this compound is "useful in perfume compositions as a modifier for ionones and methyl ionones, in modern-aldehydic creations, in perfumes with fruity-alkehydic topnotes, in combination with vetiver or woody-floral perfume materials, etc.". Arctander further states that the compound is "used in flavors—in traces—for imitation raspberry and pineapple". Arctander further states that is compound is produced from citral by condensation with allyl acetone, followed by cyclization.

There is a need to produce such allyl alpha and beta ionones in an inexpensive manner and in high purity whereby they can be more readily used in augmenting or enhancing the organoleptic properties of consumable materials.

The Claisen rearrangement of allylic ethers is well documented in the literature. Thus, Denmark et al, J. Am. Chem. Soc. 1982, 104, 4972 entitled "Carbanion-accelerated Claisen Rearrangements" discloses the reaction:

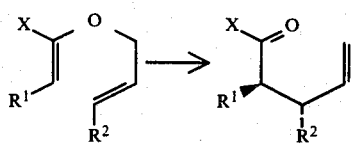

wherein X could represent alkyl and $R^1$ and $R^2$ can be the same or different methyl or hydrogen.

Daub, et al, "Tetrahedron Letters", 1983, 24(41), at pages 4397–4400, entitled "Ketal Claisen Rearrangements of Functionalized Ketals" (abstracted at Chem. Abstracts, Volume 100, 1984, No. 67808W) discloses the reaction:

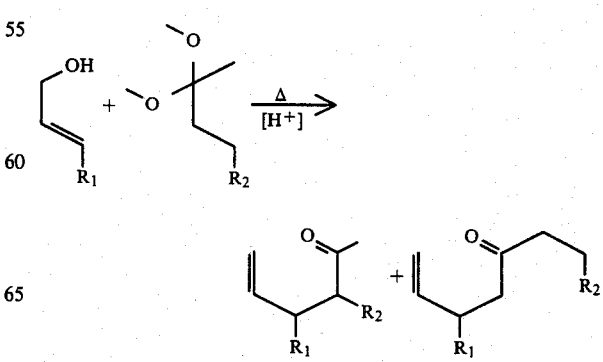

taking place in the presence of propionic acid as a catalyst wherein $R_1$ represents phenyl or n-propyl and $R_2$ represents methoxycarbonyl, methoxyacetyl or ethenyl. Daub, et al, discloses that in all cases the product having the structure:

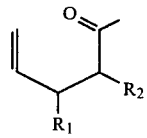

is in the majority as opposed to the compound having the structure:

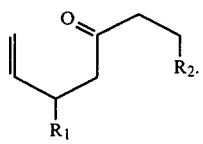

Hurd and Pollack, J. Am. Chem. Soc. 60, 1938, page 1905 discloses the reactions:

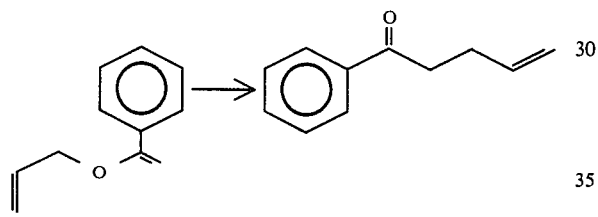

and

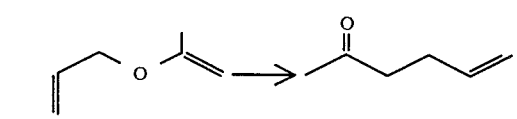

and the Merck Index, 10th edition, 1983, discloses the "Claisen" Rearrangement", to wit:

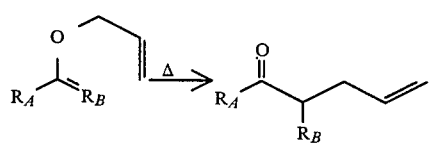

The above-mentioned "Claisen" rearrangement was originally disclosed in Ber. 45, 3157 (1912), to wit:

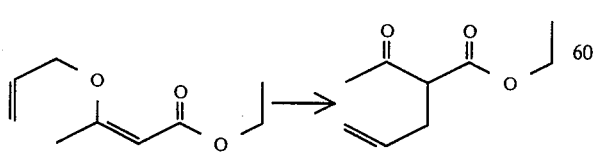

Nothing in the prior art, however, indicates the selectivity of the rearrangement of a member of the genus of compounds defined according to the structure:

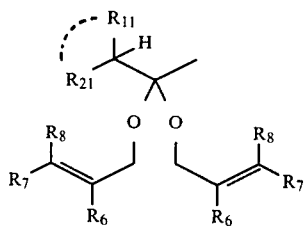

to a corresponding member of the genus of compounds having the structure:

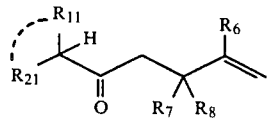

over a corresponding member of the genus of compounds having the structure:

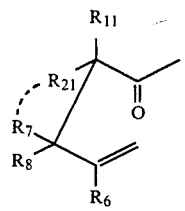

in the presence of a basic catalyst at a pH in the range of from about 7 up to about 11 in all cases except those involving the Claisen rearrangement of compounds belonging to the genus defined according to the structure:

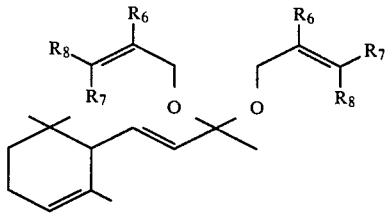

or in the presence of an acidic catalyst at a pH in the range of from about 2 up to about 6.5 in the case of the rearrangement of a member of the genus defined according to the structure:

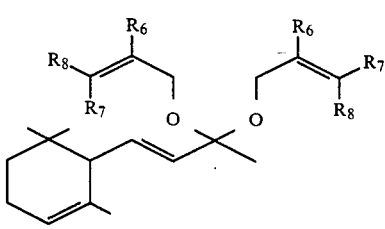

to a member of the genus defined according to the structure:

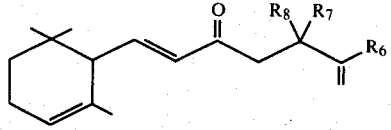

over a member of the genus defined according to the structure:

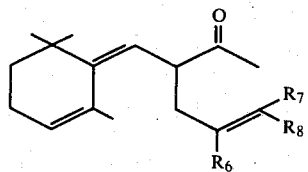

wherein $R_6$, $R_7$ and $R_8$ are defined, supra.

Chemical compounds which can provide galbanum-like, woody, piney, floral, green, herbaceous, chypre-like, sweet, fruity, raspberry-like, jasmin, rosey, pear-like, licorice-like, aniseed-like and bark-like aroma profiles with jasmin, green, cedarwood, minty, citrusy, lemony and camphoraceous topnotes are highly desirable in the art of perfumery. Many of the natural materials which provide such fragrances and contribute such desired nuances to perfumery compositions and perfumed articles are high in cost, unobtainable at times, vary in quality from one batch to another and/or are generally subject to the usual variations in natural products.

There is, accordingly, a continuing effort to find synthetic materials which will replace, enhance or augment the fragrance notes provided by natural essential oils or compositions thereof. Unfortunately, many of the synthetic materials either have the desired nuances only to a relatively small degree or they contribute undesirable or unwanted odor to the compositions.

Our invention fulfills the need for production of allyl alpha and beta ionones as well as 1-pentenoyl cyclohexane derivatives and other such asymmetrical ketones by the creation of syntheses of such asymmetric ketones inexpensively and directed towards the creation of specific derivatives.

Our invention also fulfills the need for production of materials having the above-identified aroma nuances including perfume compositions, colognes and perfumed articles which include but are not limited to solid or liquid anionic, cationic, nonionic and zwitterionic detergents, fabric softener compositions, fabric softener articles and perfumed polymers.

BRIEF DESCRIPTION OF THE DRAWINGS

FIG. 1 is the NMR spectrum for fraction 9 of the distillation of the reaction product of Example I containing the compound having the structure:

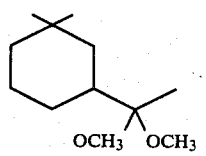

(Conditions: Field strength: 100 MHz; solvent: $CFCl_3$)

FIG. 2 is the NMR spectrum for the compound having the structure:

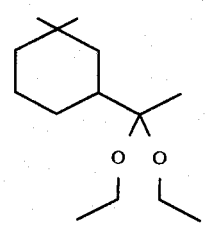

produced according to Example II (Conditions: Field strength: 100 MHz; solvent: $CFCl_3$).

Figure 3:
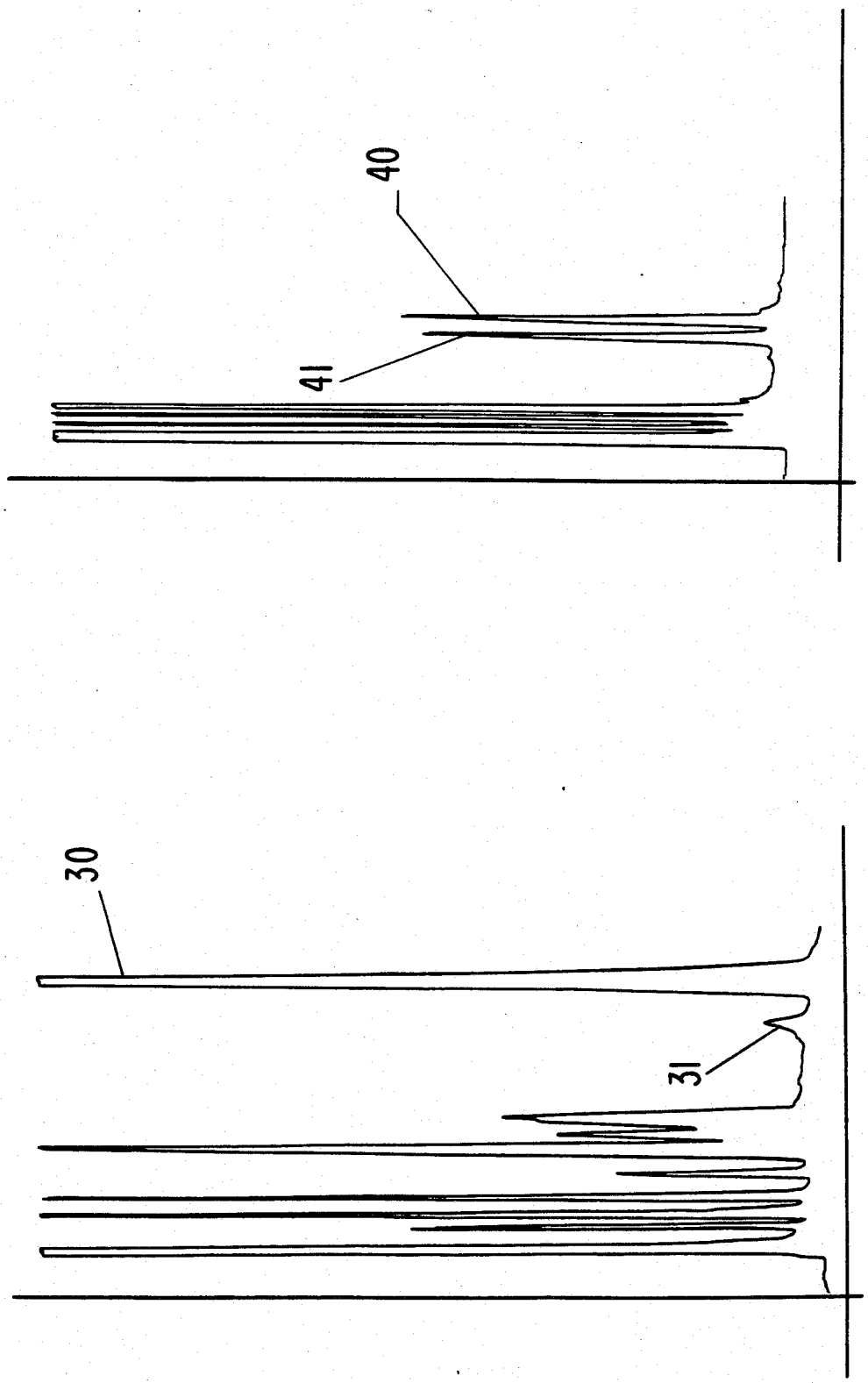

FIG. 3 is the GLC profile for the crude reaction product of Example IV containing the compounds having the structures:

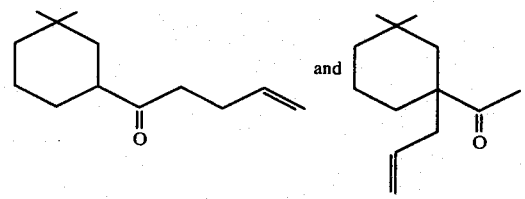

Figure 4:
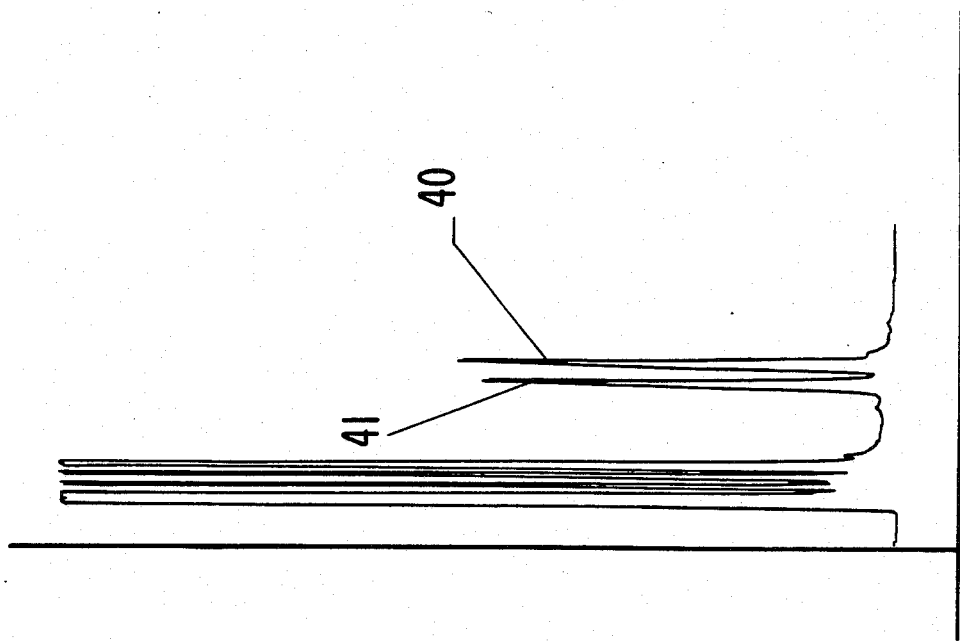

FIG. 4 is the GLC profile for the bulked fractions 9-20 of the distillation of the reaction product of Example V containing the compounds having the structures:

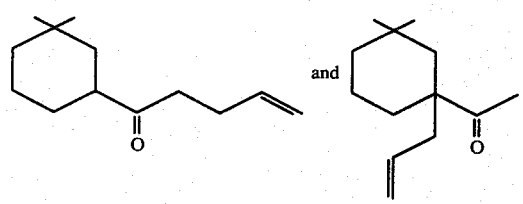

Figure 5:
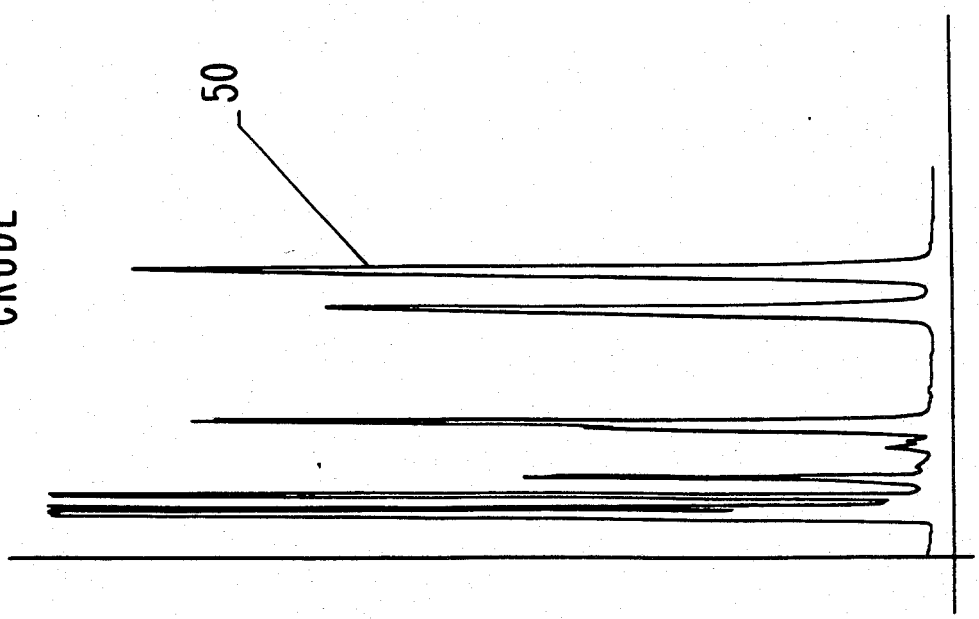

FIG. 5 is the GLC profile for the crude reaction product of Example VI(c) containing the compound having the structure:

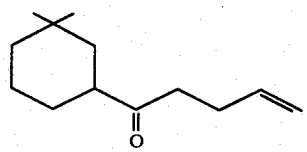

Figure 6:
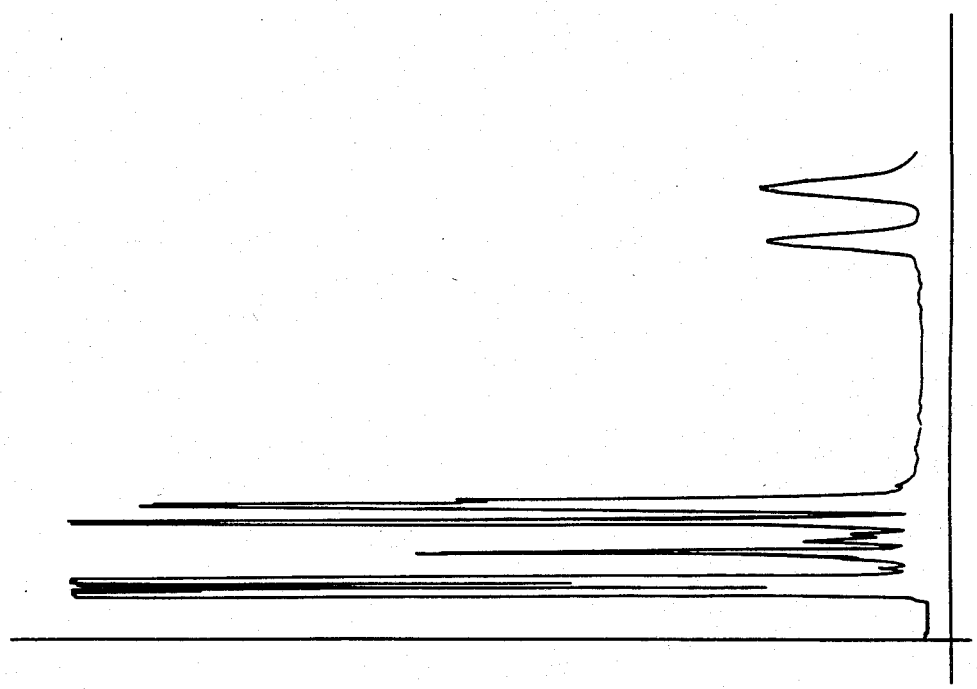

FIG. 6 is the GLC profile for the crude reaction product of Example VII containing the compounds having the structures:

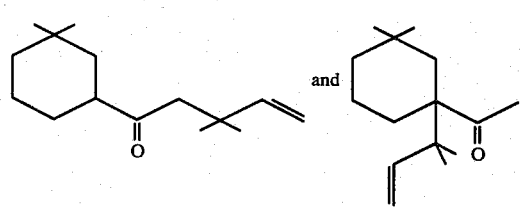

Figure 7:
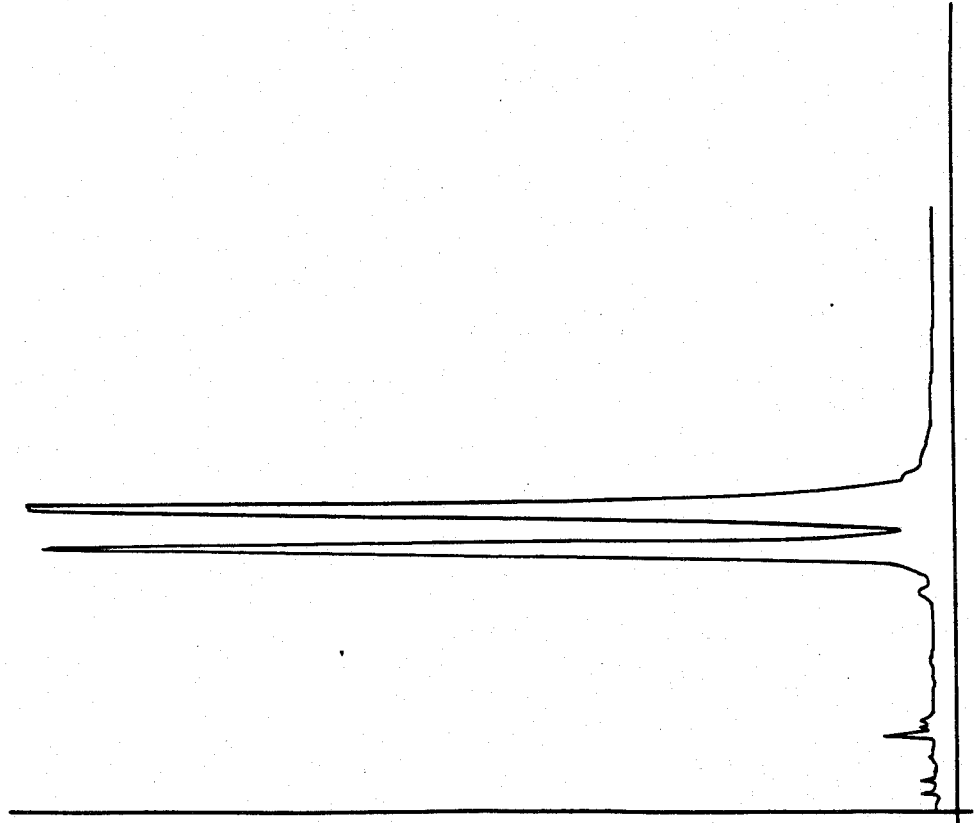

FIG. 7 is the GLC profile for fraction 6 of the distillation of the reaction product of Example VII containing the compounds having the structures:

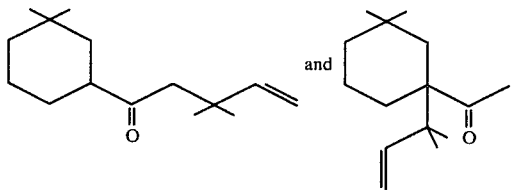

and

FIG. 8 is the NMR spectrum for fraction 5 of the distillation of the reaction product of Example VII containing the compounds having the structures:

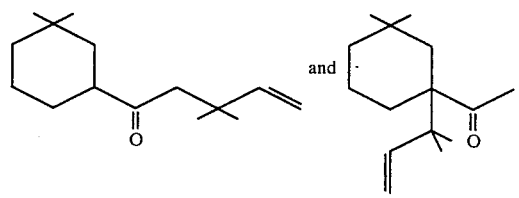

and (Solvent: CFCl₃; field strength: 100 MHz).

Figure 9:
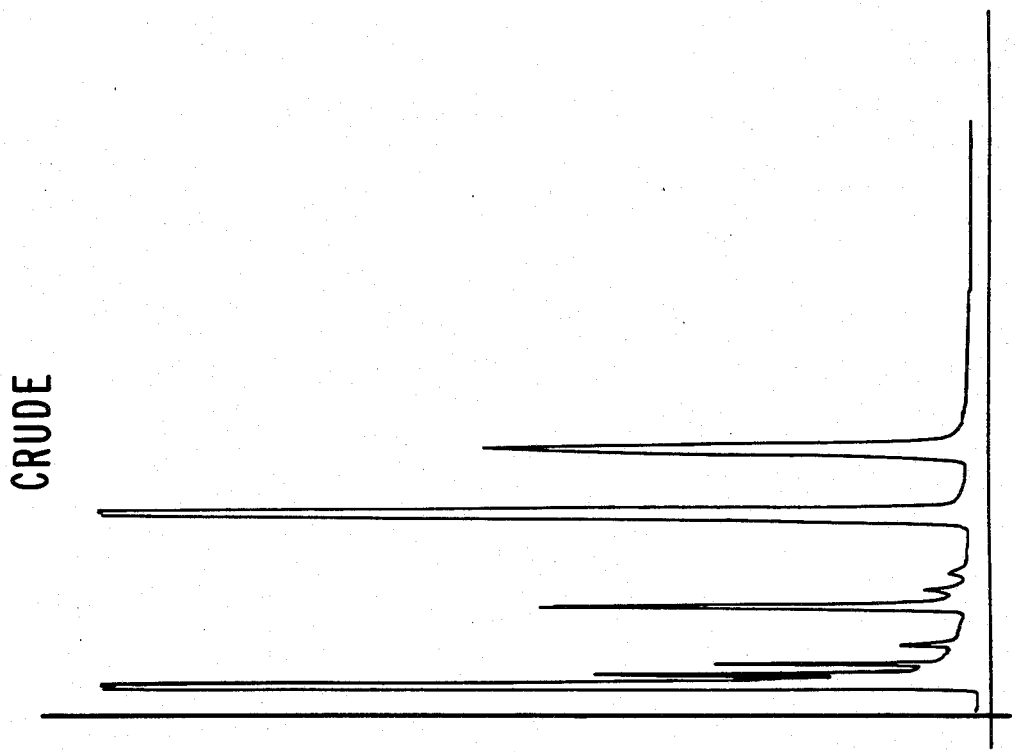

FIG. 9 is the GLC profile for the crude reaction product of Example VIII containing the compounds having the structures:

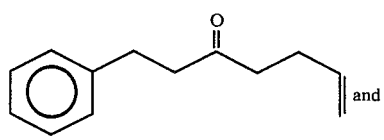

and

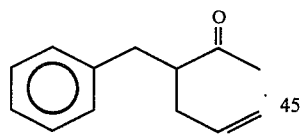

Figure 10:
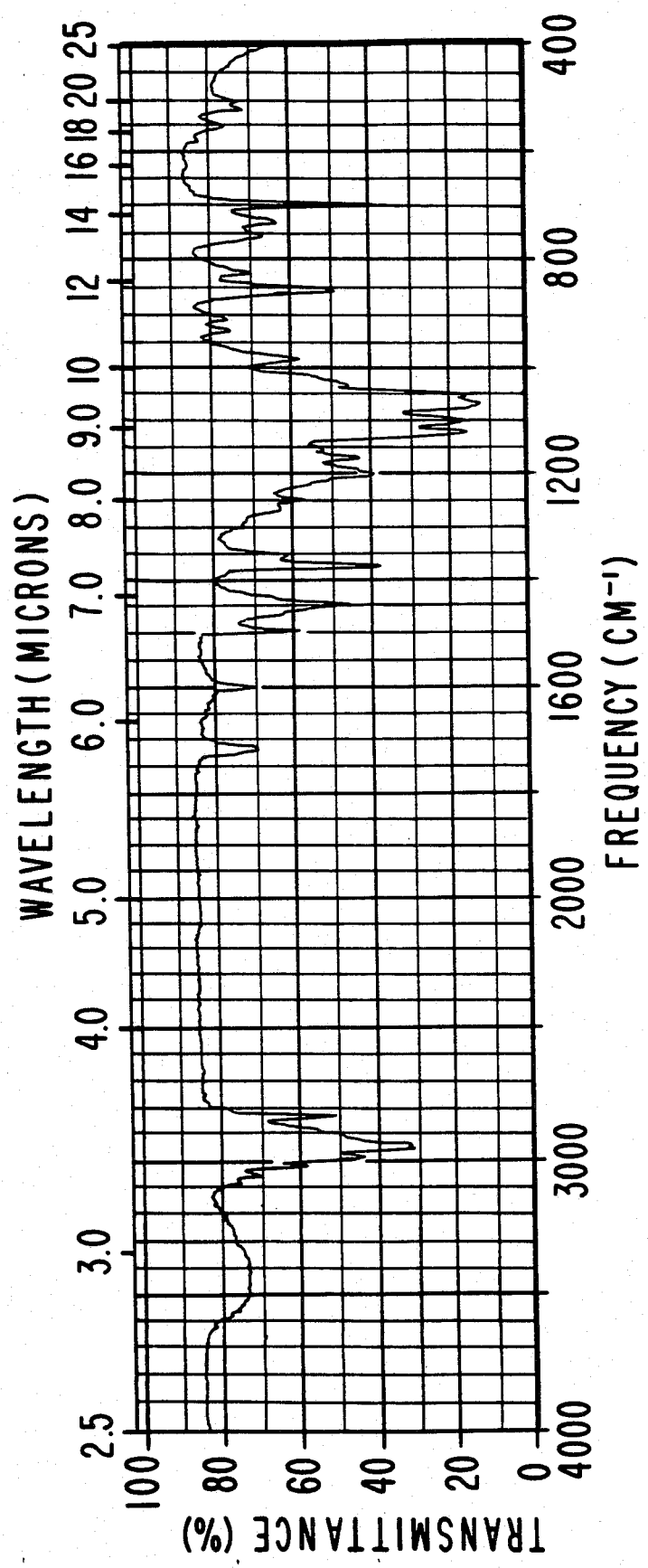

FIG. 10 is the infra-red spectrum for the compounds having the structures:

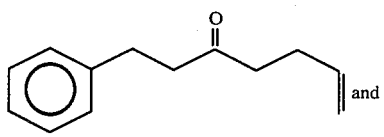

and

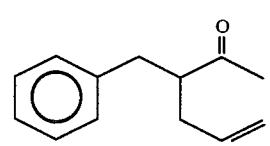

produced according to Example VIII.

Figure 11:
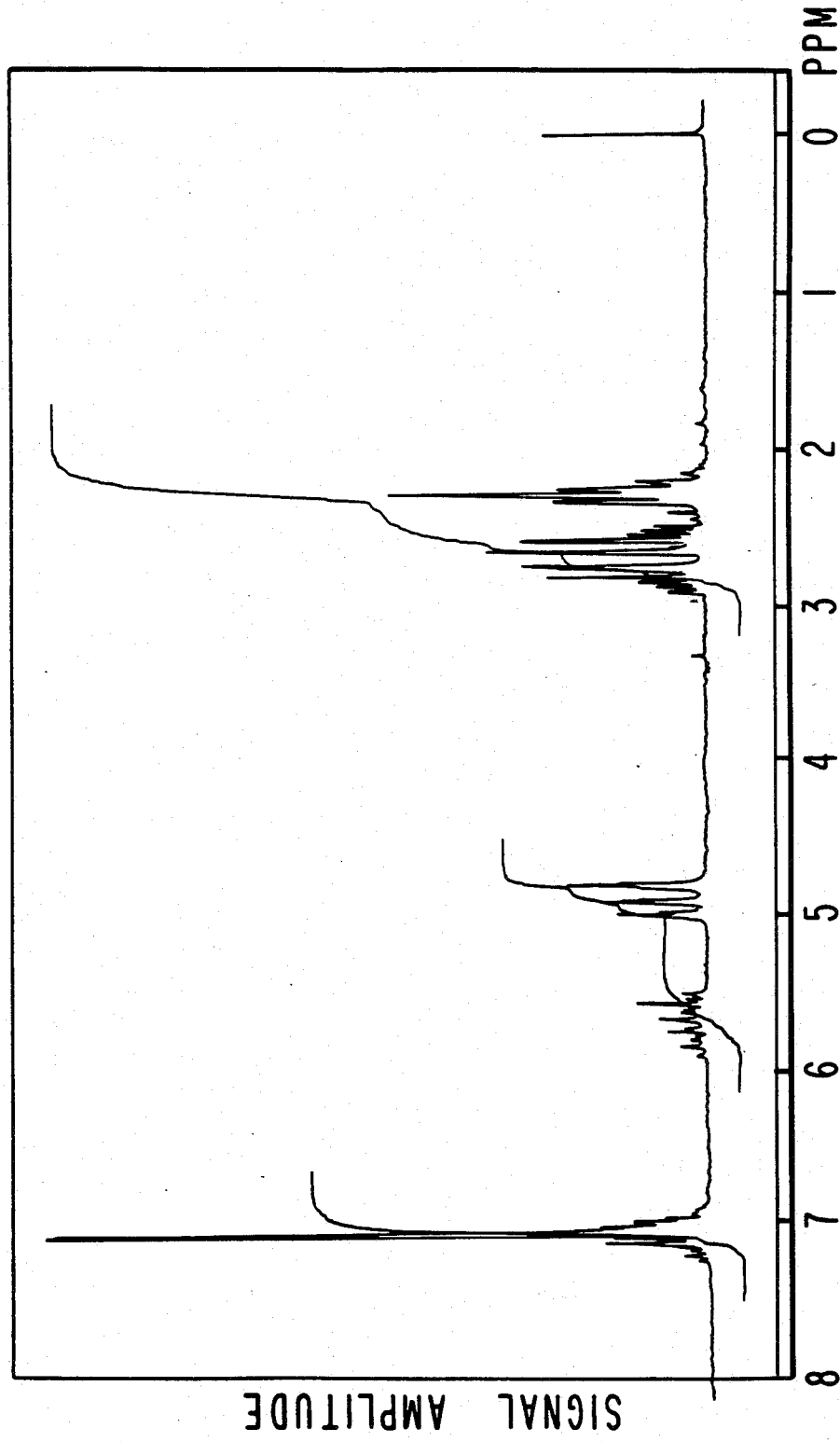

FIG. 11 is the NMR spectrum for fraction 19 of the distillation of the reaction product of Example VIII containing the compound having the structure:

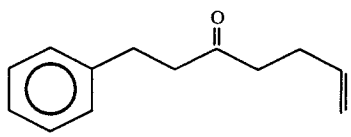

(Conditions: Field strength: 100 MHz; solvent: CFCl₃).

Figure 12:
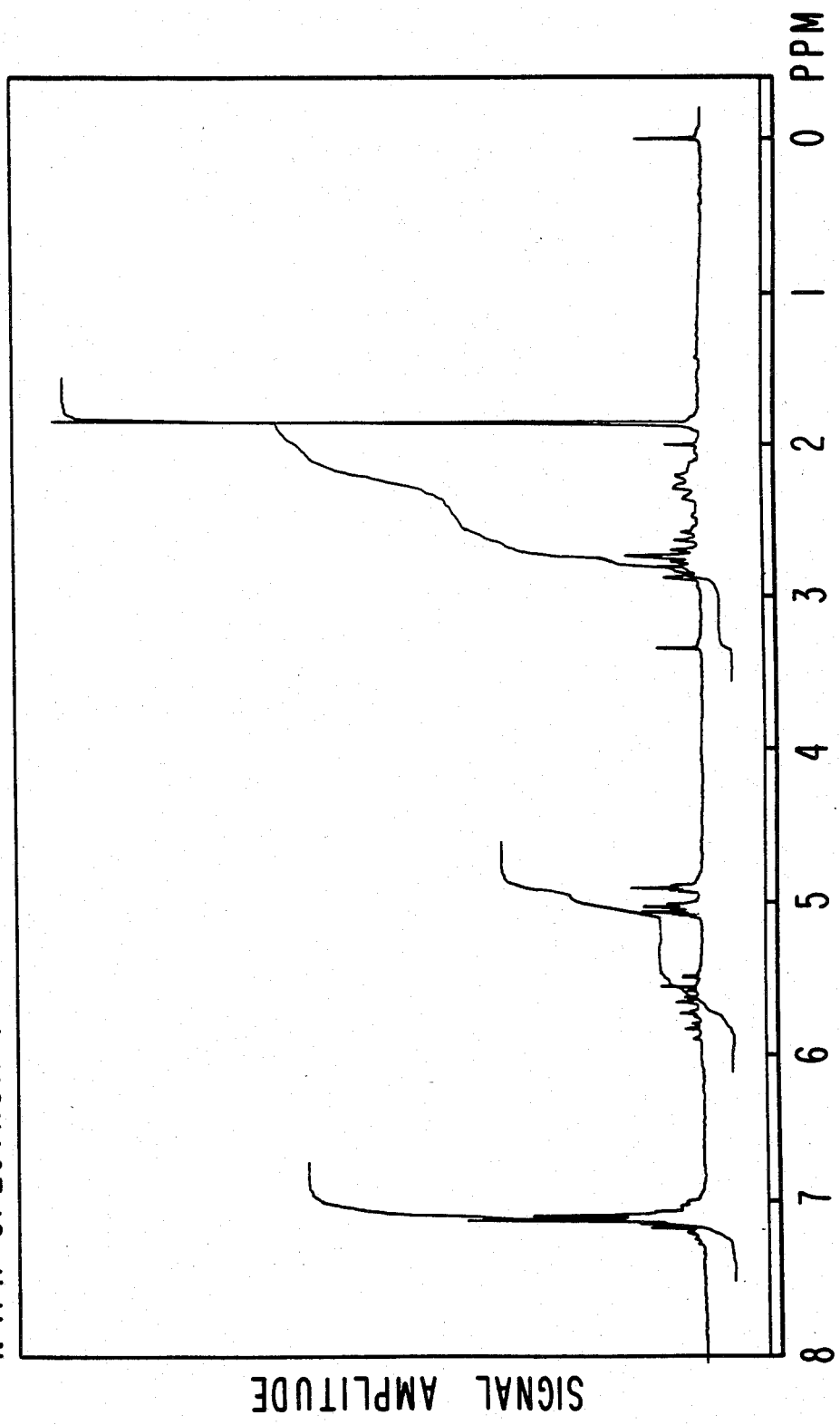

FIG. 12 is the NMR spectrum for fraction 8 of the distillation of the reaction product of Example VIII containing the compound having the structure:

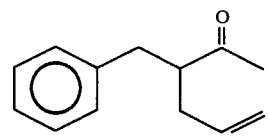

(Conditions: Field Strength: 100 MHz; solvent: CFCl₃).

Figure 13:
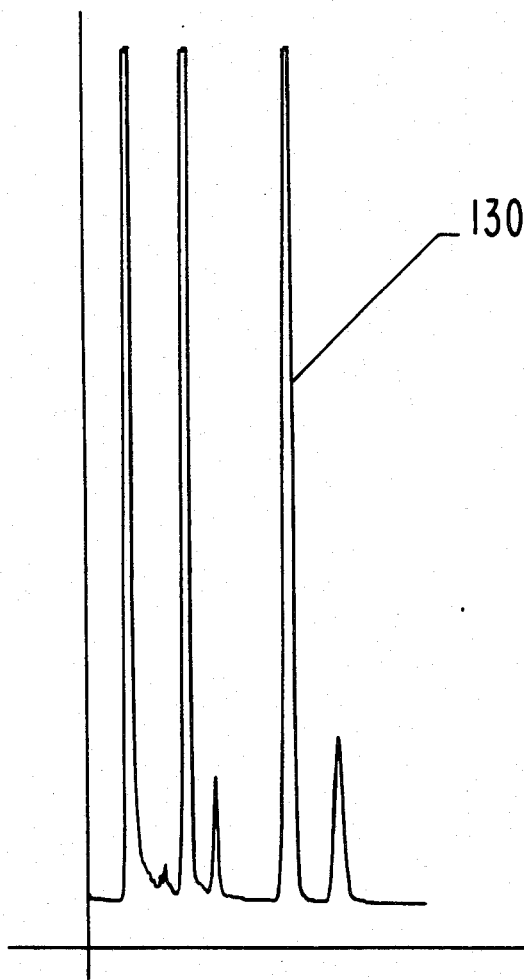

FIG. 13 is the GLC profile for the crude reaction product of Example IX containing the compounds having the structures:

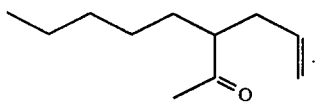

and

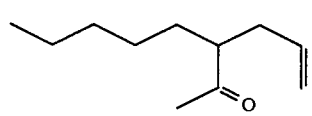

FIG. 14 is the NMR spectrum for fraction 10 of the distillation of the reaction product of Example IX containing the compound having the structure:

(Conditions: Field strength: 100 MHz; solvent: CFCl₃).

Figure 15:
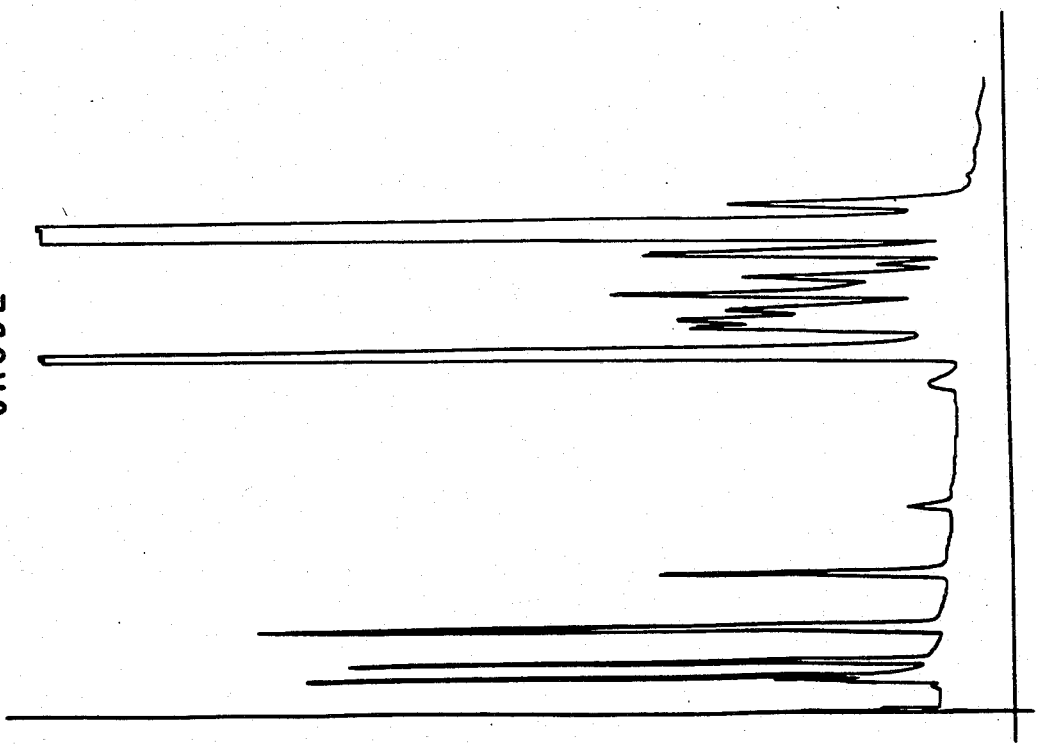

FIG. 15 is the GLC profile for the crude reaction product of Example X(A) containing the compounds having the structures:

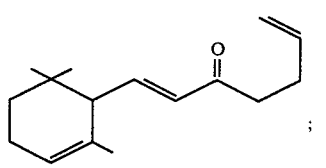

;

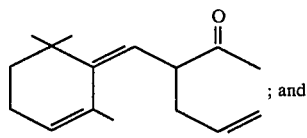

; and

Figure 16:
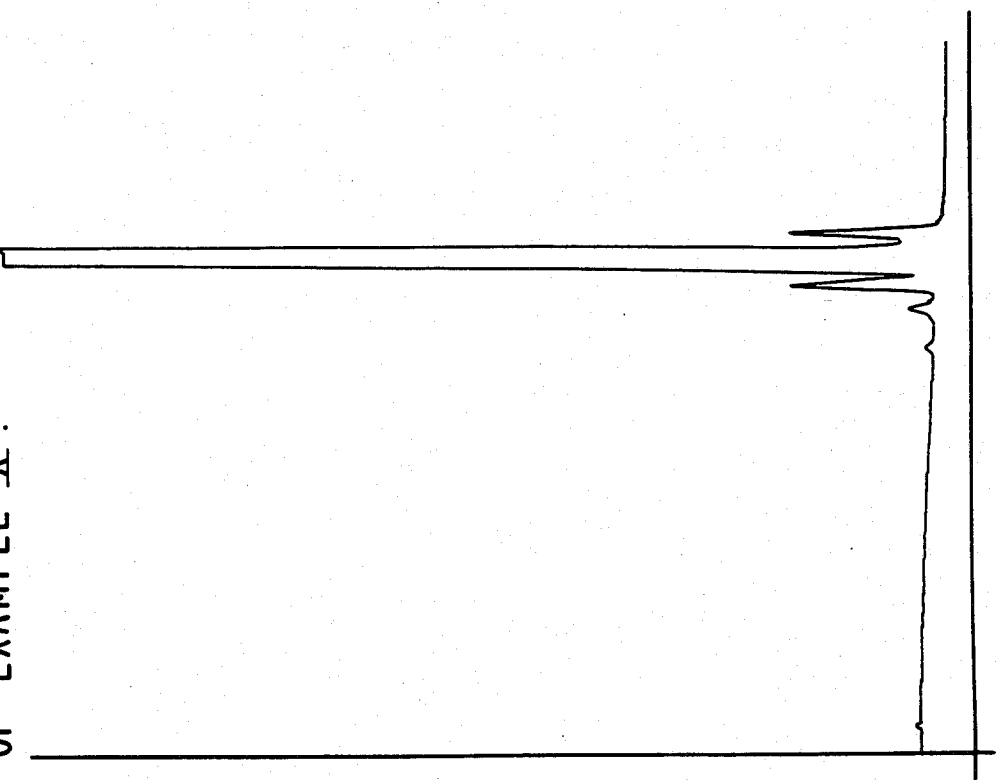

FIG. 16 is the GLC profile for bulked fractions 7–15 inclusive, for the second distillation of the reaction product of Example X(A) containing the compounds having the structures:

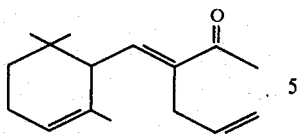

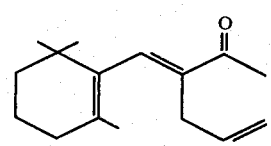

and

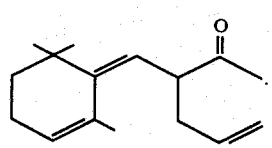

DETAILED DESCRIPTION OF THE DRAWINGS

FIG. 3 is the GLC profile for the crude reaction product of Example IV containing the compounds having the structures:

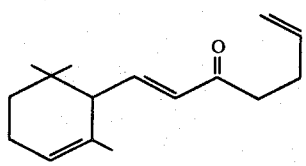

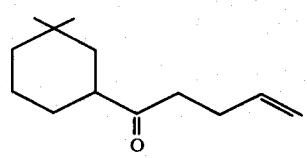 and 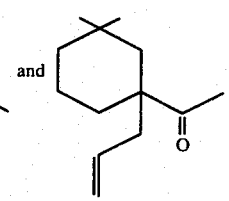

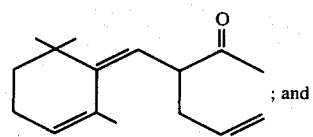 ; and

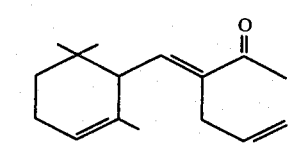

Figure 17:
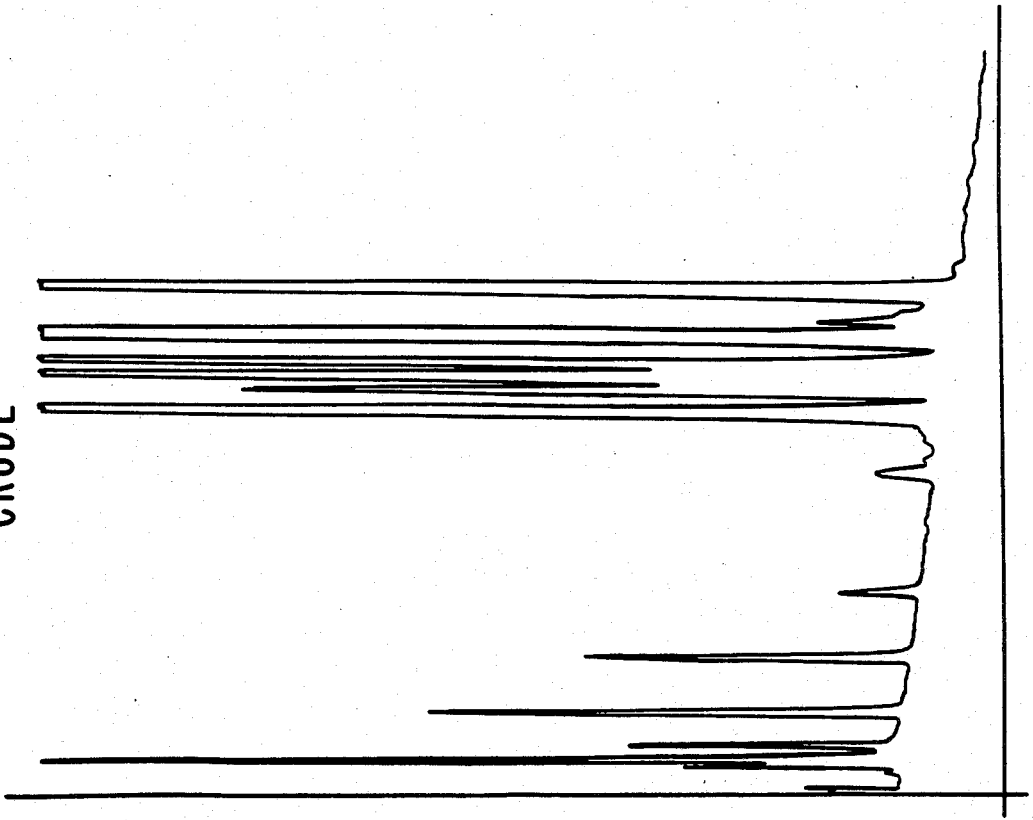

(Conditions: SE-30 column programmed at 180° C. isothermal). The peak indicated by Reference Numeral 30 is the peak for the compound having the structure:

FIG. 17 is the GLC profile for the crude reaction product of Example X(B) containing the compounds having the structures:

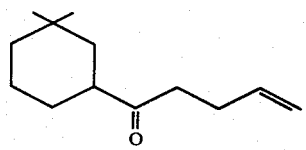

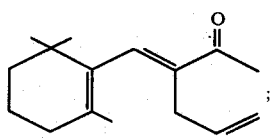 ;

The peak indicated by Reference Numeral 31 is the peak for the compound having the structure:

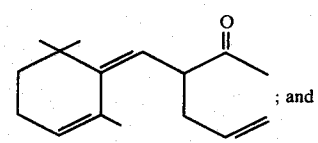 ; and

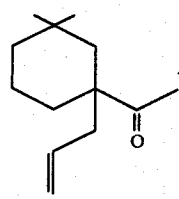

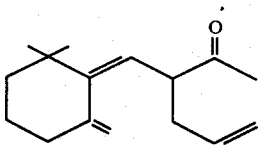

with a very minor proportion of compound having the structure:

FIG. 4 is the GLC profile for bulked fractions 9–20 of the distillation of the reaction product of Example V containing the compounds having the structures:

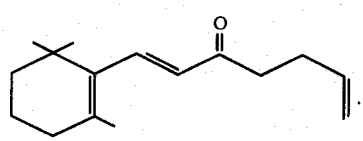

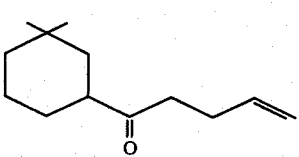 and 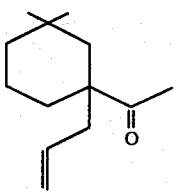

Figure 18:
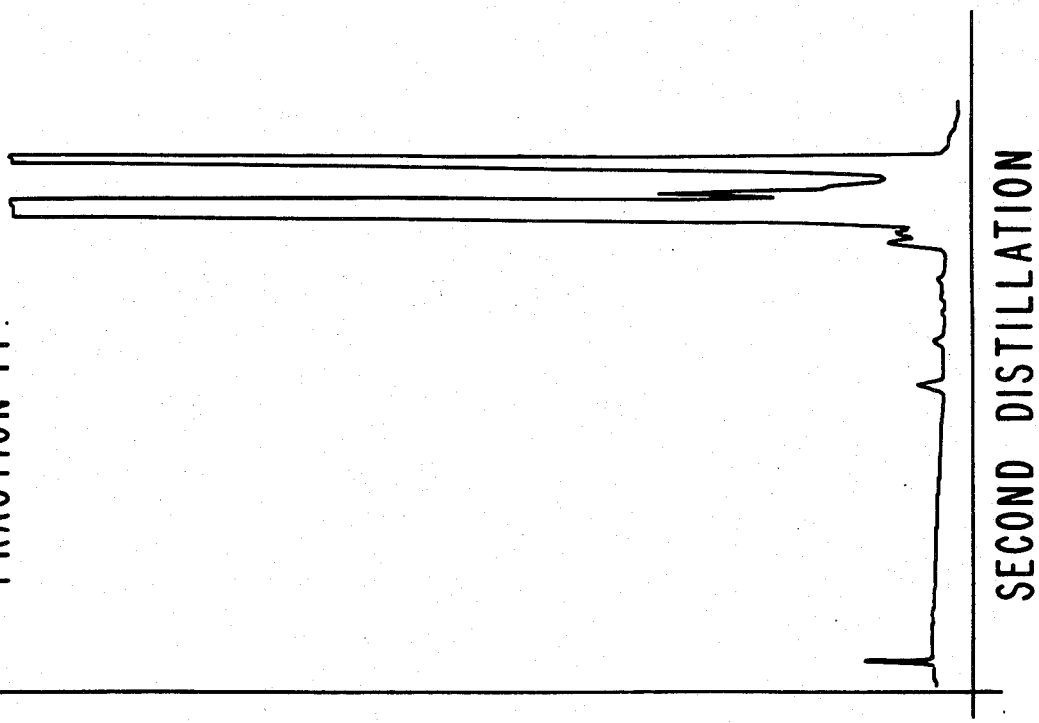

FIG. 18 is the GLC profile for fraction 14 of the second distillation of the reaction product of Example X(B) containing the compounds having the structures:

The peaks indicated by Reference Numerals 40 and 41 are the peaks for the compounds having the structures:

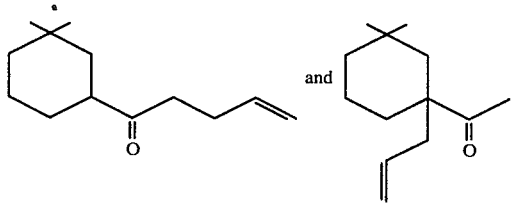

individually.

FIG. 5 is the GLC profile for the crude reaction product of Example VI(c). The peak indicated by Reference Numeral 50 is the peak for the compound having the structure:

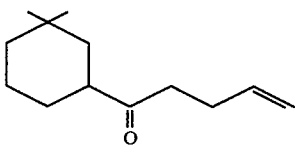

FIG. 13 is the GLC profile for the crude reaction product of Example IX containing the compounds having the structures:

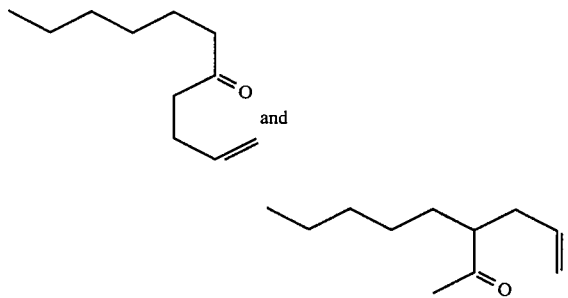

(Conditions: SE-30 column programmed at 160° C. isothermal). The peak indicated by Reference Numeral 130 is the peak for the compounds having the structures:

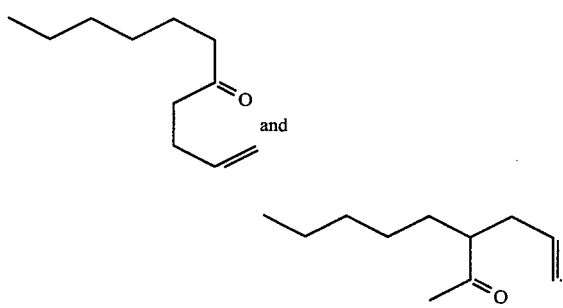

THE INVENTION

The invention broadly relates to compounds defined according to the generic structure:

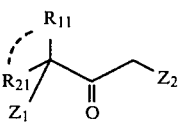

wherein one of $Z_1$ or $Z_2$ is the moiety:

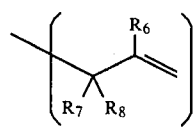

and the other of $Z_1$ or $Z_2$ represents hydrogen; wherein $R_{11}$ and $R_{21}$ represents hydrogen or the same or different alkyl or alkenyl with the proviso that $R_{11}$ and $R_{21}$ are not both hydrogen or $R_{11}$ and $R_{21}$ taken together:

(i) complete a cycloalkyl, cycloalkenyl, bicycloalkyl, mono or polyalkyl cycloalkyl, mono or polyalkyl cycloalkenyl ring, or (ii) represent alkylidene, cycloalkenyl alkylidene, aralkylidene, mono or polyalkyl cycloalkenyl alkylidene or mono or polyalkyl aralkylidene;

and wherein $R_6$, $R_7$ and $R_8$ are the same or different and each represents hydrogen or methyl.

Broadly, our invention relates to a process for producing the compounds defined according to the genus:

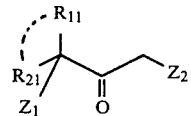

which are hereinafter referred to as "asymmetric ketones". Such a process is an "isomer-directed process" which involves a Claisen rearrangement of diallylic ethers which in turn are produced by means of reacting an allylic alcohol with a dialkyl ketal of a ketone.

More specifically, the asymmetric ketones of our invention generically defined according to the structure:

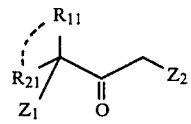

are prepared by first reacting a ketone defined according to the structure:

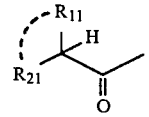

wherein $R_{11}$ and $R_{21}$ are defined, supra, with a trialkylorthoformate defined according to the structure:

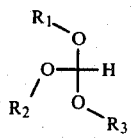

wherein $R_1$, $R_2$ and $R_3$ are the same or different and each represents $C_1$-$C_3$ lower alkyl according to the reaction:

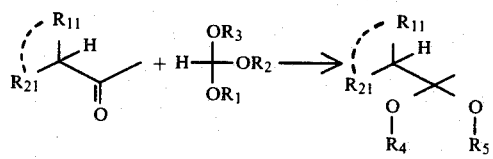

whereby the compound having the structure:

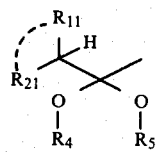

is formed wherein $R_4$ and $R_5$ are each one of $R_1$, $R_2$ and $R_3$. The resulting dialkyl ketal defined according to the structure:

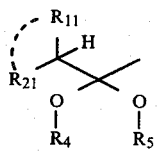

may then be used "as is" for its perfumery properties or for augmenting or enhancing the aroma of the perfume composition, cologne or perfumed article, e.g., solid or liquid anionic, cationic, nonionic or zwitterionic detergent, perfumed polymer, fabric softener composition or fabric softener article or it may be further reacted with an allyl alcohol defined according to the structure:

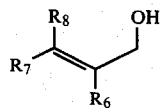

wherein $R_6$, $R_7$ and $R_8$ are as defined, supra.

This reaction takes place in the presence of an acid or base depending upon the desired ratio of ultimate asymmetric ketone desired. For producing a number of isomers specified herein, the reaction takes place using an acidic catalyst as disclosed in the prior art. See Daub, et al, cited, supra. For producing isomers covered by the generic structures:

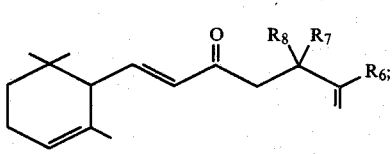

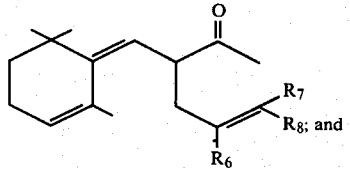

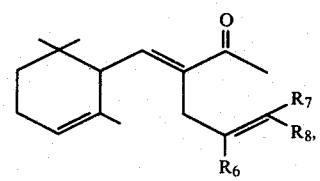

the reaction is not so disclosed.

In any event, the reaction involving the Claisen rearrangement taking place at a pH of between 7 and 11 is a novel reaction giving rise to unexpected, unobvious and advantageous results.

In the first part of the reaction of the allylic alcohol with a dialkyl ketal, the diallyl ketal defined according to the structure:

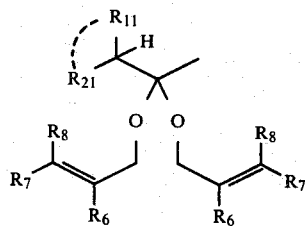

is formed.

A number of the diallyl ketals created using the foregoing process are novel.

The resulting diallyl ketal then rearranges to form two compounds which are members of the following two genera:

(i) the genus defined according to the structure:

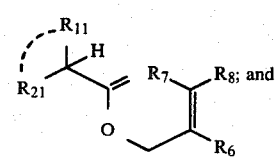

(ii) the genus defined according to the structure:

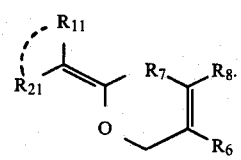

Depending upon the pH of the reaction mass during the rearrangement and the nature of $R_{11}$ and $R_{21}$ as hereinafter specified, the rearrangement forms a preponderant amount of a compound which is a member of the genus:

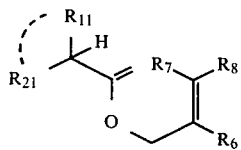

or a preponderant amount of a member of the genus having the structure:

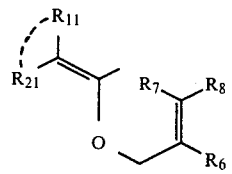

Specifically, when the reaction is carried out at a pH in the range of from about 7 up to about 11 (using, for example, sodium acetate) with the exception of that situation where the precursor ketone has the structure:

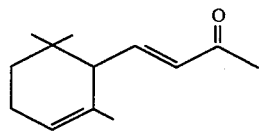

and the corresponding diallyl ketal precursor genus has the structure:

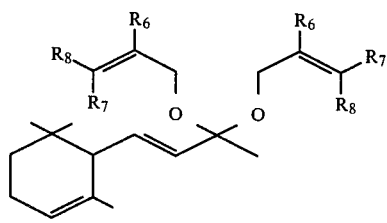

a preponderant amount of compound within the genus having the structure:

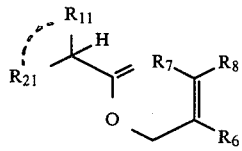

is formed.

When the reaction is carried out at a pH in the range of from about 2 up to about 6.5 (for example, using an acidic catalyst such as citric acid) with the exception of that situation where the precursor ketone has the structure:

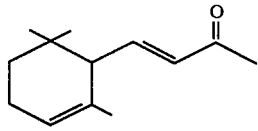

and the corresponding diallyl ketal genus has the structure:

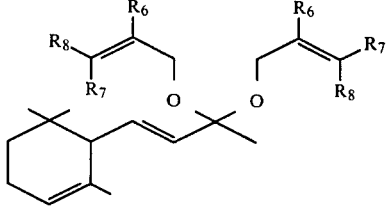

a preponderant amount of genus defined according to the structure:

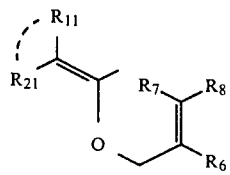

is formed.

On the contrary, when using an acidic catalyst with the precursor ketone having the structure:

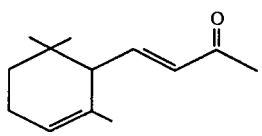

which gives rise to the diallyl ketal genus having the structure:

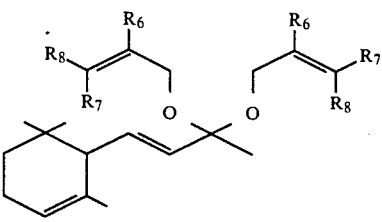

a preponderant amount of genus defined according to the structure:

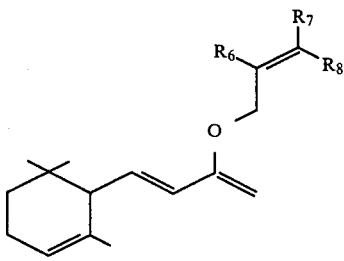

is formed.

The mechanism of the rearrangement of the compound having the structure:

is as follows:

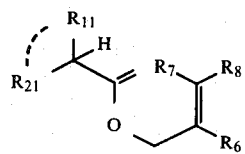

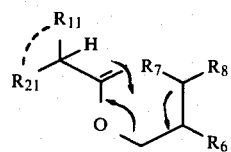

whereby the compound having the structure:

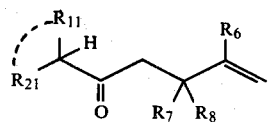

is formed.

The mechanism of the rearrangement of the compound having the structure:

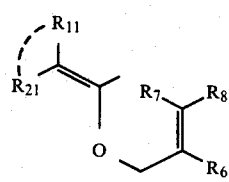

is thusly:

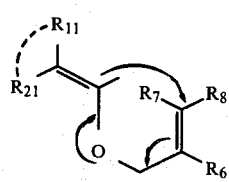

whereby the compound having the structure:

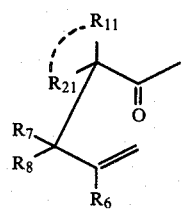

is formed.

In summary, the reaction of the allylic alcohol with a dialkyl ketal to form the diallyl ketal is thusly:

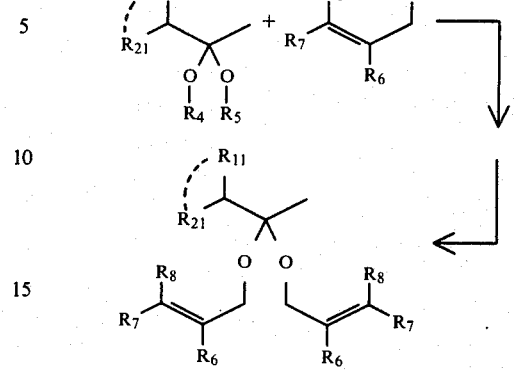

With the exception stated, supra, concerning the diallyl ketal genus defined according to the structure:

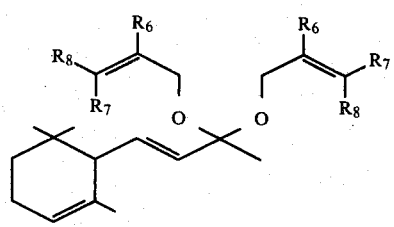

the rearrangement of the diallyl ketal follows the following reaction course (preponderantly) in a reaction mass at a pH of from 7 up to about 11 (basic) thusly:

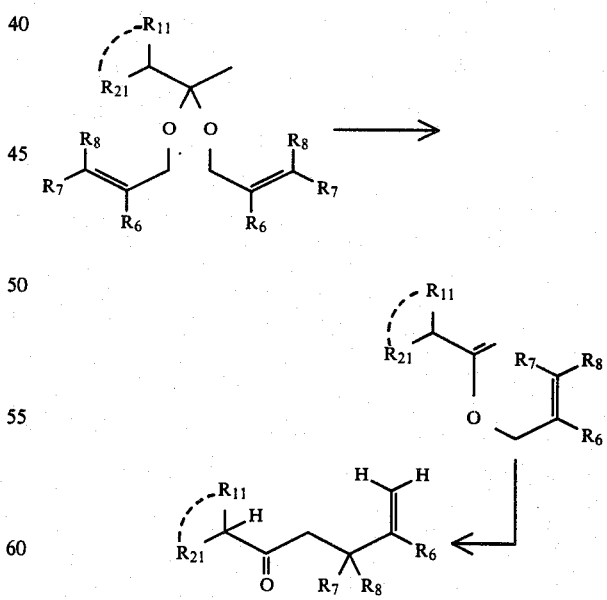

With the exceptions stated, supra (and exemplified in Example X(A), infra), the reaction sequence is preponderantly as follows in an acidic reaction medium, e.g., using a propionic or citric acid catalyst:

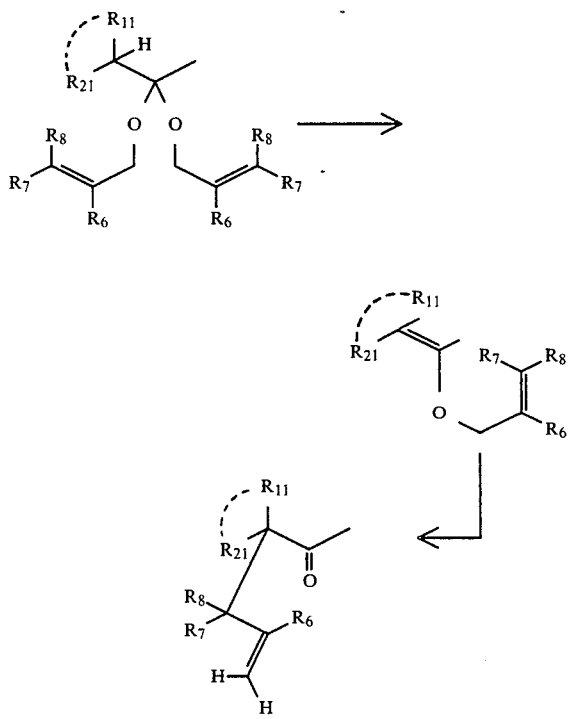

In the reaction to form the dialkyl ketal, to wit:

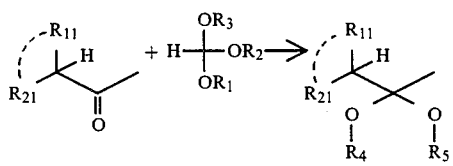

the reaction temperature is in the range of from about −10° C. up to about 50° C.

The mole ratio of ketone having the structure:

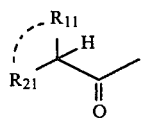

to trialkylorthoformate having the structure:

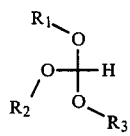

is from about 1:1 up to about 1:2.

When using an acid catalyst, various acids can be used, e.g., propionic acid, citric acid, hydrochloric acid, or any other Lewis or protonic acid. The preferred mole percent of acid catalyst is from about 0.01 mole percent up to about 0.10 mole percent but when using an acidic catalyst the pH of the reaction mass including that existing during the Claisen rearrangement must be between about 2 and about 6.5.

When using a basic medium, the preferred basic catalyst is an alkali metal alkanoate, for example, sodium acetate, potassium acetate, potassium formate, sodium formate, sodium propionate, potassium propionate, sodium butyrate or potassium butyrate. The mole percent of base in the reaction mass may vary from about 0.01 percent up to about 0.40 mole percent, but when using a basic catalyst, the reaction mass must be maintained at a pH of between 7 and 11.

In carrying out the reaction to form the dialkyl ketal, all the reagents are charged to the reaction mass and the alkyl formate, formed by reaction, is removed by means of distillation. The organic phase is washed and dried over a molecular sieve or anhydrous magnesium sulfate. The crude ketal may be used "as is" for its perfumery properties or it may be further reacted with the allylic alcohol defined according to the structure:

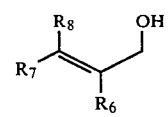

according to the reaction:

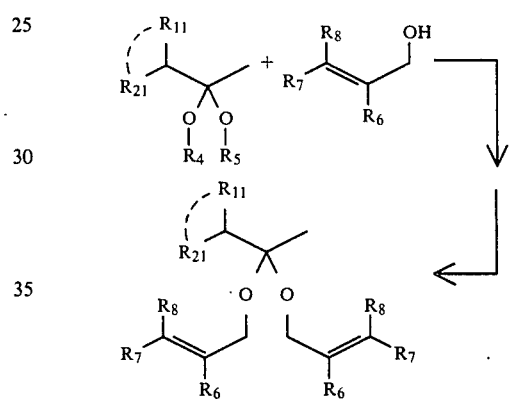

The thus-formed diallyl ether is preferably not isolated but remains in the reaction mass and is rearranged via the Claisen rearrangement (in acidic or basic media, as desired) according to the reactions:

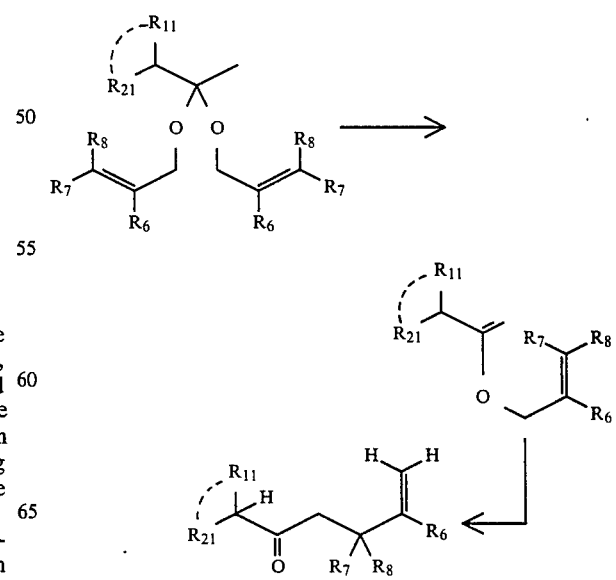

-continued
and

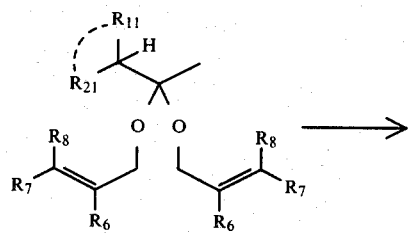

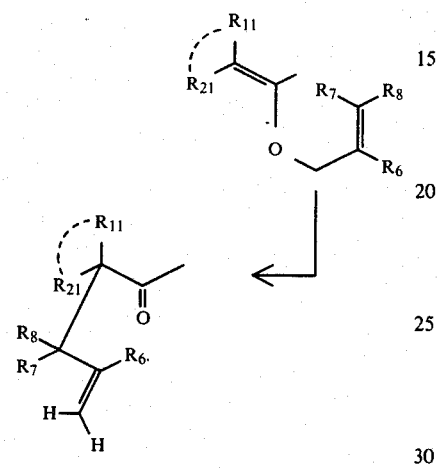

The mole ratio of dialkyl ketal defined according to the structure:

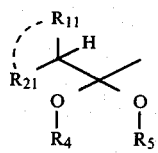

to allylic alcohol defined according to the structure:

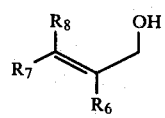

may vary from about 1:1 up to about 1:3 with a mole ratio of dialkyl ketal:allylic alcohol of about 1:2 being preferred.

The reaction temperature may vary from about 120° C. up to 220° C. with a reaction temperature of about 150° C. being preferred.

Following the rearrangement reaction, the reaction mass is preferably not washed but distilled directly with the allylic alcohol defined according to the structure:

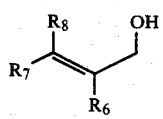

being recycled.

As an example of the application of the foregoing reaction conditions, when the reaction of our invention takes place with a rearrangement of the diallylic ether defined according to the structure:

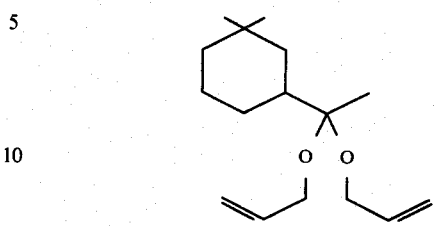

at 150° C., two compounds are formed, the first having the structure

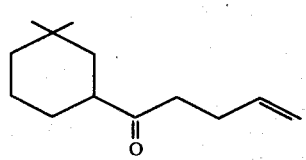

and the second having the structure:

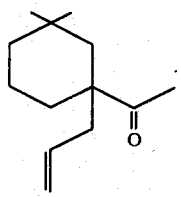

When using the citric acid catalyst, the mole ratio of the compound having the structure:

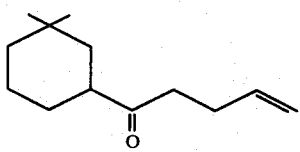

to the compound having the structure:

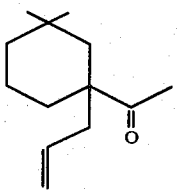

is 1:4. When using no catalyst, the mole ratio of compound having the structure:

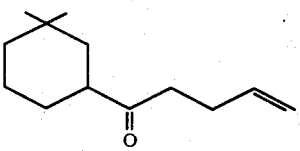

to the compound having the structure:

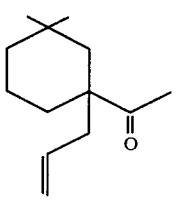

is 4:6. When using the sodium acetate catalyst the mole ratio of the compound having the structure:

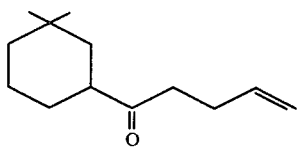

to the compound having the structure:

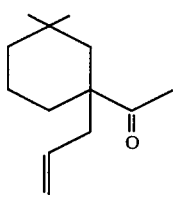

is 20:1.

Another example of the application of the foregoing reaction conditions when the reaction of our invention takes place with a rearrangement of the diallylic ether defined according to the structure:

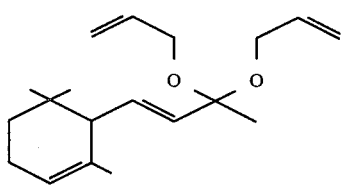

at 150° C., three compounds are formed, now the first having the structure:

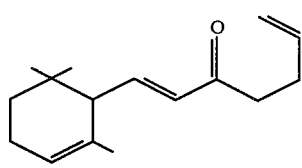

the second having the structure:

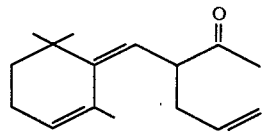

and the third having the structure:

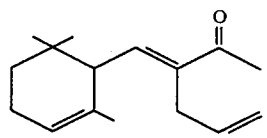

When using the citric acid catalyst, the mole ratio of the compound having the structure:

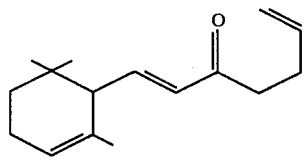

to the sum total of compounds having the structures:

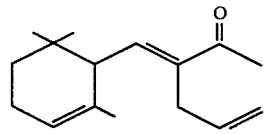

and

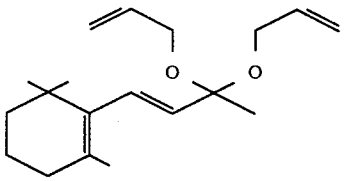

is about 48:1.

On the contrary, an additional example of the application of the foregoing reaction conditions exists when the reaction of our invention takes place with a rearrangement of the diallylic ether defined according to the structure:

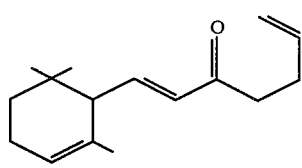

at 150° C. where four compounds are formed, the first having the structure:

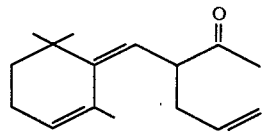

the second having the structure:

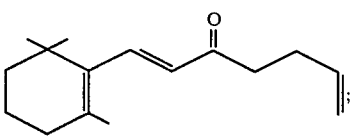

the third having the structure:

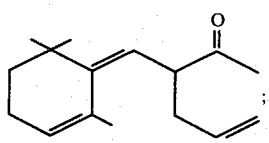

and the fourth having the structure:

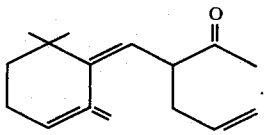

When using the citric acid catalyst, compounds having the structures:

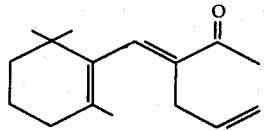

and

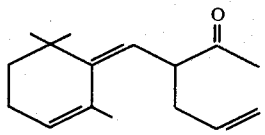

are predominant in the reaction mass and compounds having the structures:

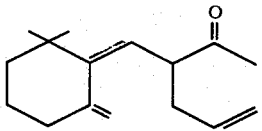

and

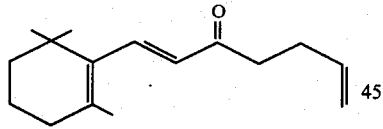

are present in the reaction mass in very small quantities.

Examples of compounds produced according to our process and their organoleptic properties are as follows:

TABLE I

| COMPOUND STRUCTURE | PERFUMERY PROPERTIES |
|---|---|
| Compound having the structure: 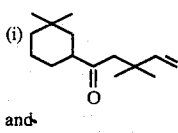 | A galbanum-like, floral, green, herbaceous and chypre aroma profile. |
| Mixture of compounds having the structures: (i) ... and ... | A woody, piney, floral aroma with citrusy, lemony topnotes. |

TABLE I-continued

| COMPOUND STRUCTURE | PERFUMERY PROPERTIES |
|---|---|
| (ii) ... the mole ratio of (i) to (ii) being 1:4. | |
| Mixture of compounds having the structures: (i) ... and (ii) ... the mole ratio of (i) to (ii) being being 1:4. | A sweet, fruity, raspberry-like, jasmin, floral and rosey aroma with jasmin topnotes. |
| Compound having the structure: ... OCH₃ OCH₃ | A sweet, pear and fruity aroma with green, cedarleaf and minty topnotes. |
| Mixture of compounds having the structures: (i) ... and (ii) ... the mole ratio of (i) to (ii) being 1:4. | A licorice and aniseed aroma with fruity, pineapple, green, woody, herbaceous, minty and camphoraceous topnotes. |
| Mixture of compounds having the structures: (i) ...; (ii) ...; and (iii) ... with the mole ratio of (i) to the sum total of (ii) and (iii) being 48:1 | A sweet, floral, fruity, bark-like and green aroma profile. |

The asymmetric ketones and ketals of our invention and one or more auxiliary perfume ingredients including, for example, alcohols, aldehydes, ketones other than the asymmetric ketones of our invention, ketals other than the asymmetric ketals of our invention, terpinic hydrocarbons, nitriles, esters, lactones, natural essential oils and synthetic essential oils, may be admixed so that the combined odors of the individual components produce a pleasant and desired fragrance, particularly and preferably in galbanum, jasmin and floral fragrances.

Such perfume compositions usually contain:

(a) the main note or the "bouquet" or foundation stone of the composition;

(b) modifiers which round off and accompany the main notes;

(c) fixatives which include odorous substances which lend a particular note to the perfume throughout all stages of evaporation and substances which retard evaporation; and (d) topnotes which are usually low boiling fresh smelling materials.

In perfume compositions, it is the individual olfactory components which contribute to their particular olfactory characteristics, however, the overall sensory effect of the perfume composition will be at least the sum total of the effects of each of the ingredients. Thus, the asymmetric ketones and ketals of our invention can be used to alter, modify or enhance the aroma characteristics of a perfume composition, for example, by utilizing or moderating the olfactory reaction contributed by another ingredient in the composition.

The amount of asymmetric ketones and ketals of our invention which will be effective in perfume compositions as well as in perfumed articles and colognes, depends upon many factors, including the other ingredients, their amounts and the effects which are desired. It has been found that perfume compositions containing as little as 0.01% of the asymmetric ketones and/or ketals or even less (e.g., 0.005%) can be used to impart galbanum-like, woody, piney, floral, green, herbaceous, chypre, sweet, fruity, raspberry-like, jasmin, rosey, licorice, aniseed and bark-like aromas with jasmin, green, cedarleaf, minty, citrusy, lemony, fruity, pineapple, woody, herbaceous and camphoraceous topnotes to soaps, cosmetics, solid or liquid anionic, cationic, nonionic or zwitterionic detergents, perfumed polymers or other products. The amount employed can range up to 70% of the fragance components and will depend upon the considerations of cost, nature of the end product, the effect desired on the finished product and the particular fragrance sought.

The asymmetric ketones and/or ketals of our invention are useful as olfactory components in detergents and soaps, space odorants and deodorants, perfumes, colognes, toilet water, bath preparations, such as lacquers, brilliantines, pomades and shampoos; cosmetic preparations, such as creams, deodorants, hand lotions and sun screens; powders, such as talcs, dusting powders, face powders and the like. When used as an olfactory component in a perfumed article as little as 0.1% of the asymmetric ketone or ketal will suffice to impart intense galbanum-like, woody, piney, floral, green, herbaceous, chypre, sweet, fruity, raspberry-like, jasmin, rosey, pear-like, licorice, aniseed-like and bark-like aroma profiles with jasmin, green, cedarleaf, minty, citrusy, lemony, fruity, pineapple, woody, herbaceous and camphoraceous topnotes to various galbanum, rose, floral and jasmin formulations. Generally, no more than 3% of the asymmetric ketone or ketal based on the ultimate end product is required in the perfumed article. Thus, the range of use of the asymmetric ketones and/or ketals of our invention in perfumed articles may vary from 0.1% up to about 3%.

In addition, the perfume composition or fragrance composition of our invention can contain a vehicle or carrier for the asymmetric ketones or ketals of our invention. The vehicle can be a liquid, such as an alcohol, such as ethy alcohol, a glycol, such as propylene glycol or the like. The carrier can also be an absorbant solid, such as a gum (e.g., gum arabic, guar gum and xanthan gum) or components for encapsulating the composition (such as gelatin when encapsulation is carried on by means of coacervation, or such as a urea formaldehyde prepolymer when a urea formaldehyde polymer wall is formed around a perfumed scenter).

The following examples serve to illustrate our invention and the invention is to be considered restricted thereto only as indicated in the appended claims.

All parts and percentages given are by weight unless otherwise specified.

EXAMPLE I

FORMATION OF DIMETHYL KETAL OF 1-ACETYL-3,3-DIMETHYL CYCLOHEXANE

Reaction

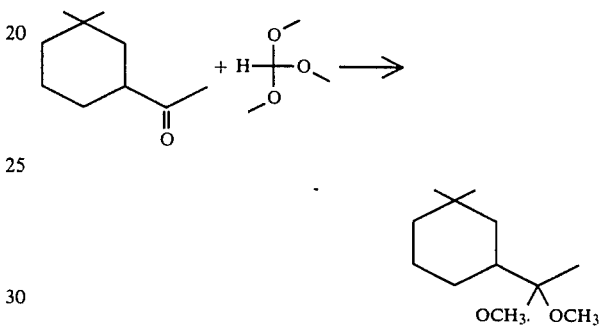

Into a 12 liter reaction flask equipped with stirrer, thermometer, reflux condenser, bidwell collection trap and heating mantle are place 1848 grams of 1-acetyl-3,3-dimethyl cyclohexane and 24 ml. concentrated hydrochloric acid.

Over a period of 10 minutes, 1908 grams of trimethylorthoformate is added to the reaction mass while maintaining the temperature at 23°-37° C. The reaction mass is then heated after the addition to a temperature in the range of 80°-90° C. and maintained at that temperature for a period of three hours. At the end of the three hour period 50 grams of sodium acetate is added to the reaction mass. The reaction mass is stirred and 1 liter of water is added. The organic layer is separated from the aqueous layer and the organic layer is distilled on a 12"×1" Goodloe column yielding the following fractions:

| FRACTION NO. | VAPOR TEMP. (°C.) | LIQUID TEMP. (°C.) | VACUUM mm/Hg. PRESSURE |
|---|---|---|---|
| 1 | 35/55 | 70/82 | 4.0/4.0 |
| 2 | 55 | 87 | 4.0 |
| 3 | 60 | 87 | 4.0 |
| 4 | 65 | 88 | 4.0 |
| 5 | 73 | 90 | 4.0 |
| 6 | 73 | 90 | 4.0 |
| 7 | 73 | 90 | 4.0 |
| 8 | 73 | 90 | 4.0 |
| 9 | 73 | 90 | 4.0 |
| 10 | 73 | 90 | 4.0 |
| 11 | 73 | 110 | 4.0 |
| 12 | 50 | 225 | 1.0 |

FIG. 1 is the NMR spectrum for fraction 9 of the foregoing distillation containing the compound having the structure:

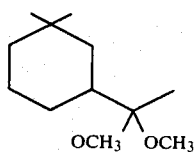

(Conditions: CFCl₃ solvent; 100 MHz field strength).

The resulting product has an excellent sweet, pear, fruity aroma profile with green, cedarleaf and minty topnotes.

EXAMPLE II

PREPARATION OF DIETHYL KETAL OF 1-ACETYL-3,3-DIMETHYL CYCLOHEXANE

Reaction

Into a 5 liter reaction flask equipped with stirrer, thermometer, reflux condenser, bidwell trap apparatus, addition funnel and heating mantle are placed 1232 grams of 1-acetyl-3,3-dimethyl cyclohexane and 18 ml. concentrated hydrochloric acid. Over a period of one hour while maintaining the reaction temperature at 20°–35° C., 1480 grams of triethylorthoformate is added to the reaction mass. The reaction mass is then stirred for a period of three hours while maintaining the temperature at 90°–110° C. At the end of the three hour period the reaction mass is cooled to 20° C. and 50 grams of sodium carbonate is added. 1 Liter of water is then added and the organic phase is separated from the aqueous phase.

FIG. 2 is the NMR spectrum for the resulting product (conditions: Field strength: 100 MHz; solvent: CFCl₃).

EXAMPLE III

PREPARATION OF 1-(4-PENTENOYL)-3,3-DIMETHYL CYCLOHEXANE

Reaction

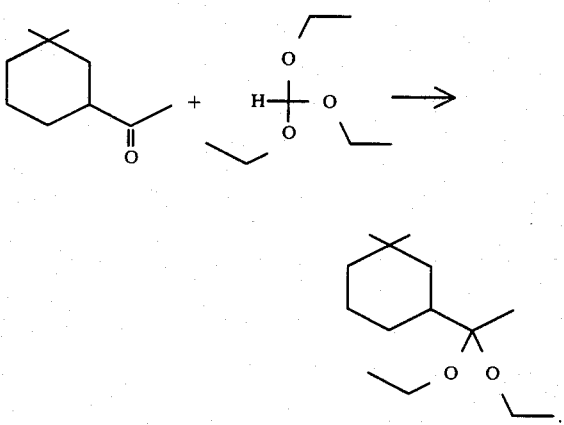

Into a 2 liter autoclave is placed 672 grams of the dimethyl ketal of 1-acetyl-3,3-dimethyl cyclohexane prepared according to Example I; 348 grams of allyl alcohol; and 15 grams of sodium acetate. The autoclave is sealed and the contents are heated to 150° C. and maintained at 150° C. for a period of five hours. At the end of the five hour period the autoclave contents are cooled and the autoclave is opened. The resulting product is distilled on a 12" Goodloe column yielding the following fractions:

| FRACTION NO. | VAPOR TEMP. (°C.) | LIQUID TEMP. (°C.) | VACUUM mm/Hg. PRESSURE |
|---|---|---|---|
| 1 | 50/50 | 80/80 | 3.0 |
| 2 | 50 | 82 | 3.0 |
| 3 | 50 | 82 | 3.0 |
| 4 | 56 | 87 | 3.0 |
| 5 | 53 | 88 | 3.0 |
| 6 | 55 | 95 | 3.0 |
| 7 | 55 | 98 | 3.0 |
| 8 | 64 | 100 | 3.0 |
| 9 | 64 | 100 | 3.0 |
| 10 | 64 | 100 | 3.0 |
| 11 | 80 | 109 | 3.0 |
| 12 | 80 | 109 | 3.0 |
| 13 | 90 | 109 | 3.0 |
| 14 | 90 | 109 | 3.0 |
| 15 | 80 | 109 | 1.6 |
| 16 | 80 | 109 | 1.6 |
| 17 | 71 | 112 | 0.8 |
| 18 | 71 | 116 | 0.8 |
| 19 | 72 | 128 | 0.8 |
| 20 | 74 | 168 | 0.8 |
| 21 | 76 | 235 | 0.8 |
| 22 | 50 | 240 | 0.8 |

The mole ratio of isomers in the reaction mass is 20:1 of the compound having the structure:

to the compound having the structure:

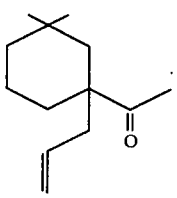

The peak indicated by Reference Numeral 30 is the peak for the compound having the structure:

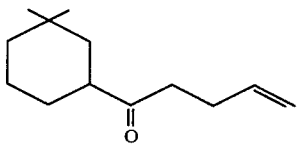

The peak indicated by Reference Numeral 31 is the peak for the compound having the structure:

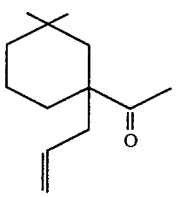

The resulting reaction mixture has an intense galbanum aroma with floral, green, herbaceous and chypre undertones.

EXAMPLE IV

PREPARATION OF 1-(4-PENTENOYL)-3,3-DIMETHYL CYCLOHEXANE

Reaction

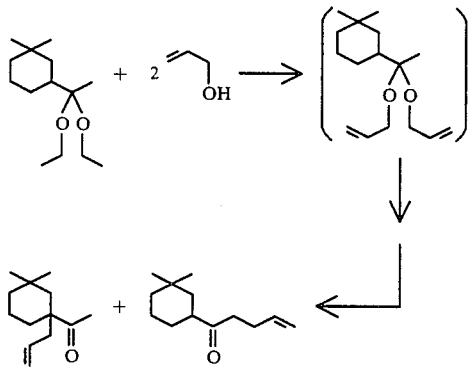

Into a 2 liter autoclave is placed 700 grams of the diethyl ketal of 1-acetyl-3,3-dimethyl cyclohexane prepared according to Example II; 360 grams of allyl alcohol; and 10 grams of sodium acetate. The autoclave is sealed and heated to 150° C. and maintained at that temperature for a period of five hours. At the end of the five hour period, the autoclave is opened and the contents are filtered, washed with water and distilled on a 12" Goodloe column yielding the following fractions:

| FRACTION NO. | VAPOR TEMP. (°C.) | LIQUID TEMP. (°C.) | VACUUM mm/Hg. PRESSURE |
|---|---|---|---|
| 1 | 47/42 | 100/91 | 1.2/9 |
| 2 | 56 | 94 | 0.9 |
| 3 | 68 | 105 | 0.9 |
| 4 | 70 | 106 | 0.9 |
| 5 | 71 | 105 | 0.9 |
| 6 | 70 | 101 | 0.85 |
| 7 | 70 | 102 | 0.85 |
| 8 | 70 | 102 | 0.85 |
| 9 | 70 | 102 | 0.85 |
| 10 | 79 | 105 | 0.9 |
| 11 | 79 | 110 | 0.9 |
| 12 | 79 | 108 | 0.8 |
| 13 | 79 | 108 | 0.8 |
| 14 | 79 | 110 | 0.8 |
| 15 | 79 | 130 | 0.8 |
| 16 | 65 | 170 | 0.8 |

FIG. 3 is the GLC profile for the crude reaction product. The peak indicated by Reference Numeral 30 is the peak for the compound having the structure:

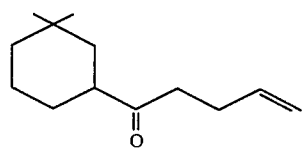

The peak indicated by Reference Numeral 31 is the peak for the compound having the structure:

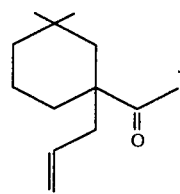

The resulting product has an intense galbanum-like, floral, green, herbaceous and chypre aroma.

The ratio of isomer having the structure:

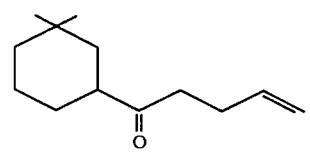

to the isomer having the structure:

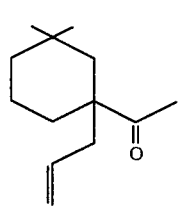

is 20:1.

EXAMPLE V

PREPARATION OF MIXTURE OF ISOMERS: 1-(4-PENTENOYL)-3,3-DIMETHYL CYCLOHEXANE AND 1-ACETYL-1-(2-PROPENYL)-3,3-DIMETHYL CYCLOHEXANE

Reaction

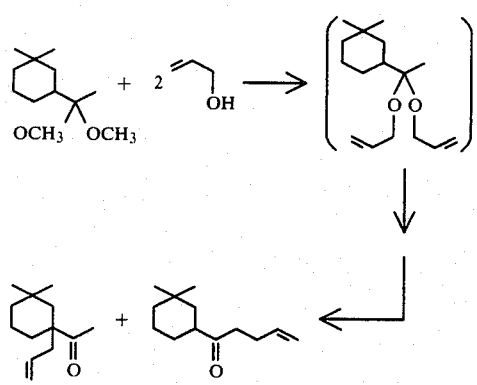

Into a 2 liter autoclave is placed 672 grams (3 moles) of the dimethyl ketal of 1-acetyl-3,3-dimethyl cyclohexane prepared according to Example I; 348 grams (6 moles) allyl alcohol; and 0.5 grams of citric acid. The autoclave is heated to 150° C. and maintained at that temperature under pressure for a period of two hours. At the end of the two hour period, the contents of the autoclave is cooled, the autoclave is opened and the contents are filtered and distilled yielding the following fractions:

| FRACTION NO. | VAPOR TEMP. (°C.) | LIQUID TEMP. (°C.) | VACUUM mm/Hg. PRESSURE |
|---|---|---|---|
| 1 | 23/58 | 23/85 | 300/200 |
| 2 | 80 | 105 | 6.0 |
| 3 | 60 | 90 | 4.0 |
| 4 | 60 | 100 | 4.0 |
| 5 | 82 | 105 | 4.0 |
| 6 | 83 | 106 | 4.0 |
| 7 | 83 | 108 | 4.0 |
| 8 | 84 | 109 | 4.0 |
| 9 | 85 | 110 | 4.0 |
| 10 | 90 | 110 | 4.0 |
| 11 | 90 | 112 | 4.0 |
| 12 | 90 | 112 | 4.0 |
| 13 | 90 | 114 | 4.0 |
| 14 | 90 | 114 | 4.0 |
| 15 | 90 | 114 | 4.0 |
| 16 | 90 | 114 | 4.0 |
| 17 | 90 | 115 | 4.0 |
| 18 | 90 | 115 | 4.0 |
| 19 | 90 | 116 | 4.0 |
| 20 | 89 | 178 | 3.0 |
| 21 | | | |

FIG. 4 is the GLC profile for the bulked fractions 9-20 of the foregoing distillation containing the compounds having the structures:

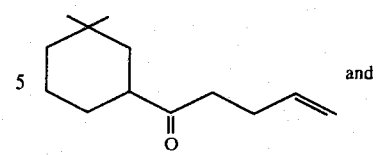

and

The isomer ratio of the compound having the structure:

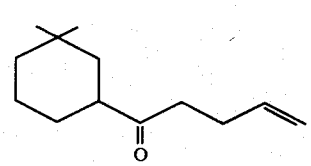

to the compound having the structure:

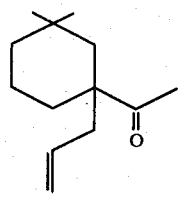

is 1:4. The resulting product has a galbanum-like, amber aroma with floral and jasmin topnotes.

EXAMPLE VI

PREPARATION OF MIXTURES OF ISOMERS OR 1-(4-PENTENOYL)-3,3-DIMETHYL CYCLOHEXANE AND 1-ACETYL-1-(2-PROPENYL)-3,3-DIMETHYL CYCLOHEXANE

Reaction

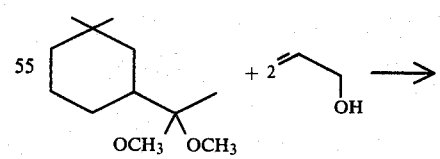

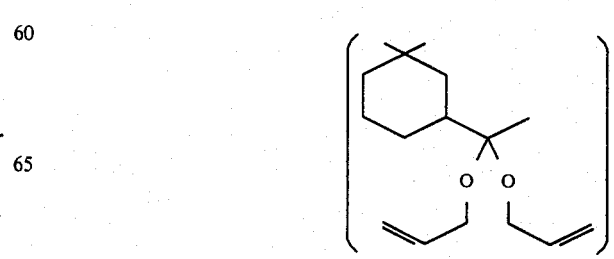

-continued

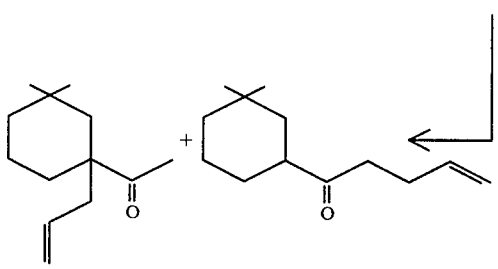

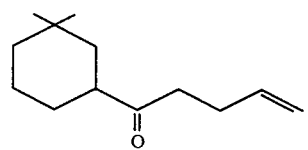

using the procedure of Example III.

TABLE II

RATIO OF ISOMER HAVING THE STRUCTURE:

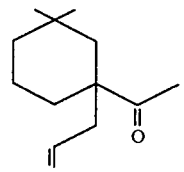

TO ISOMER HAVING THE STRUCTURE:

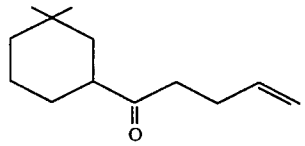

| EXAMPLE NO. | REACTANTS AND CATALYST AND AMOUNTS | REACTION CONDITIONS | |
|---|---|---|---|
| EXAMPLE VI(a) | Dimethyl ketal of 1-acetyl-3,3-dimethyl cyclohexane-672 grams<br>Citric acid-0.5 grams<br>Allyl alcohol-350 grams | 150° C. and three hours | 11:6 |
| EXAMPLE VI(b) | Dimethyl ketal of 1-acetyl-3,3-dimethyl cyclohexane-672 grams<br>Triethanolamine-10 grams<br>Diallyl alcohol-350 grams | 150° C. and six hours | 3:2 |
| EXAMPLE VI(c) | Dimethyl ketal of 1-acetyl-3,3-dimethyl cyclohexane-672 grams<br>Catalyst: NONE<br>Allyl alcohol-350 grams | 150° C. and six hours | 12:17 |
| EXAMPLE VI(d) | Dimethyl ketal of 1-acetyl-3,3-dimethyl cyclohexane-672 grams<br>Sodium carbonate-10 grams<br>Allyl alcohol-350 grams | 150° C. and six hours | 12:17 |
| EXAMPLE VI(e) | Dimethyl ketal of 1-acetyl-3,3-dimethyl cyclohexane-672 grams<br>Sodium acetate-10 grams<br>Allyl alcohol-350 grams | 150° C. and six hours | 1:20 |

The following Table II sets forth reactants including catalyst, reaction conditions and ratio of isomer having the structure:

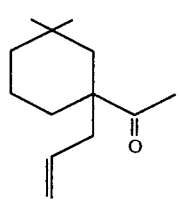

to isomer having the structure:

FIG. 5 is the GLC profile for the crude reaction product of Example VI(c). The peak indicated by Reference Numeral 50 is the peak for the compound having the structure:

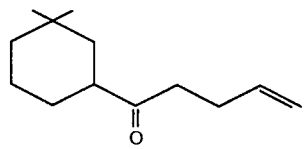

EXAMPLE VII

Preparation of mixture of
1-(3,3-DIMETHYL-4-PENTENOYL)-3,3-DIMETHYL CYCLOHEXANE and

1-ACETYL-1-(1,1-DIMETHYL-2-PROPENYL)-3,3-DIMETHYL CYCLOHEXANE

Reaction

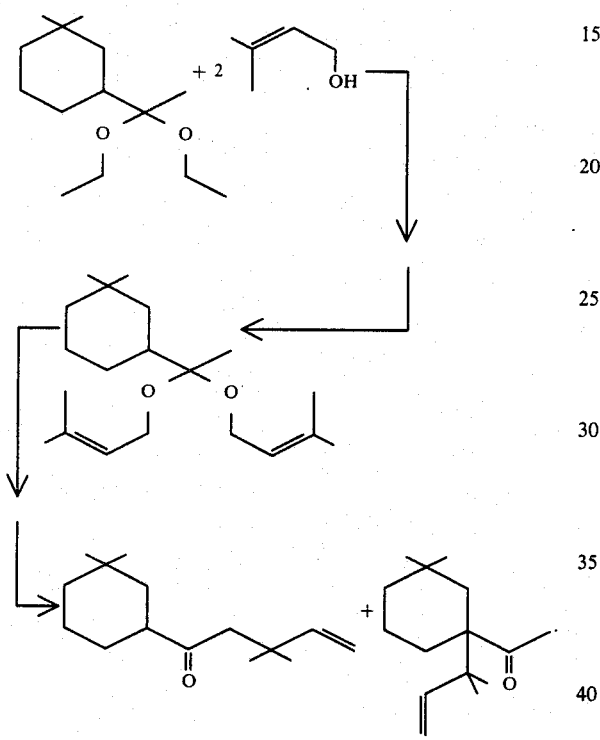

Into a 2 liter autoclave is placed 400 grams of the diethyl ketal of 1-acetyl-3,3-dimethyl cyclohexane prepared according to Example II; 516 grams of prenol; and 0.5 grams of citric acid. The autoclave is sealed and heated to 150° C. under pressure and maintained at 150° C. for a period of two hours. At the end of the two hour period the autoclave is cooled, opened and the contents are filtered and distilled on a 12" Goodloe column yielding the following fractions:

| FRACTION NO. | VAPOR TEMP. (°C.) | LIQUID TEMP. (°C.) | VACUUM mm/Hg. PRESSURE |
|---|---|---|---|
| 1 | 70/80 | 116/110 | 5.0/1.0 |
| 2 | 85 | 115 | 1.0 |
| 3 | 85 | 125 | 1.0 |
| 4 | 85 | 145 | 1.0 |
| 5 | 80 | 190 | 1.0 |
| 6 | 87 | 230 | 1.0 |

FIG. 6 is the GLC profile of the crude reaction product containing the compounds having the structures:

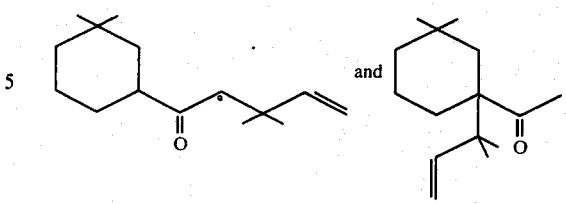

FIG. 7 is the GLC profile for fraction 6 of the foregoing distillation containing the compounds having the structures:

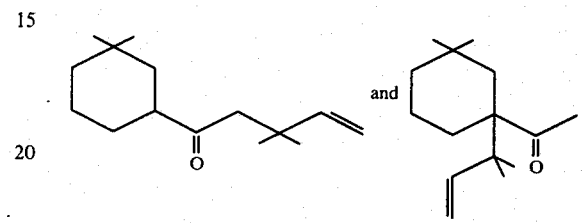

The resulting product has a woody, piney, floral aroma with citrusy and lemony topnotes.

EXAMPLE VIII

PREPARATION OF MIXTURE OF
7-PHENYL-1-HEPTEN-5-ONE

AND

4(PHENYL METHYL)1-PENTEN-5-ONE

Reactions

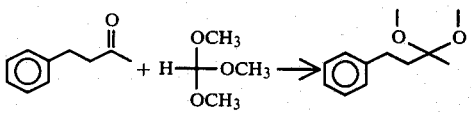

and

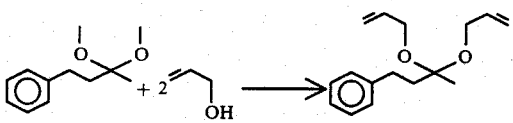

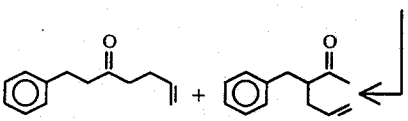

Into a 2 liter reaction flask equipped with stirrer, thermometer, reflux condenser, addition funnel, bidwell trap and heating mantel is placed 400 grams of benzyl acetone and 5 ml. concentrated hydrochloric acid. Over a period of 30 minutes, 339 grams of trimethylorthoformate is added. The reaction mass is then heated to 60° C. and maintained at 60° C. for a period of two hours with stirring.

The reaction mass is then cooled to room temperature and 10 grams of sodium carbonate is added followed by 300 ml. of water. The organic phase is separated from the aqueous phase.

The organic phase is then placed in an autoclave and 350 ml. allyl alcohol and 1 gram citric acid is added. The autoclave is sealed and heated under pressure to 150° C. The reaction mass is maintained at 150° C. under pressure in the autoclave for a period of two hours. The autoclave is then cooled, opened and the contents filtered.

The reaction mass is distilled on a 12" Goodloe column yielding the following fractions:

| FRACTION NO. | VAPOR TEMP. (°C.) | LIQUID TEMP. (°C.) | VACUUM mm/Hg. PRESSURE |
|---|---|---|---|
| 1 | 26/26 | 50/68 | 1.5 |
| 2 | 70 | 114 | 1.4 |
| 3 | 72 | 119 | 0.9 |
| 4 | 87 | 120 | 0.9 |
| 5 | 89 | 122 | 0.8 |
| 6 | 90 | 122 | 0.8 |
| 7 | 88 | 122 | 0.8 |
| 8 | 89 | 122 | 0.8 |
| 9 | 89 | 122 | 0.8 |
| 10 | 89 | 122 | 0.8 |
| 11 | 89 | 122 | 0.8 |
| 12 | 86 | 116 | 0.8 |
| 13 | 86 | 118 | 0.8 |
| 14 | 86 | 118 | 0.8 |
| 15 | 88 | 118 | 0.85 |
| 16 | 95 | 120 | 0.95 |
| 17 | 95 | 122 | 0.90 |
| 18 | 100 | 130 | 1.0 |
| 19 | 110 | 187 | 1.6 |
| 20 | 110 | 200 | 1.0 |

FIG. 9 is the GLC profile for the crude reaction product.

FIG. 10 is the infra-red spectrum for the compound having the structure:

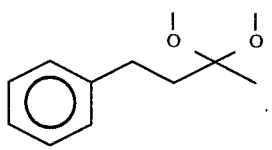

FIG. 11 is the NMR spectrum for fraction 19 of the foregoing distillation for the compound having the structure:

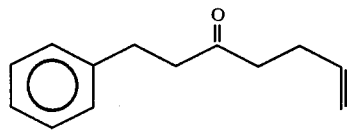

(Conditions: Field strength: 100 MHz; solvent: CFCl₃).

FIG. 12 is the NMR spectrum for fraction 8 of the foregoing distillation for the compound having the structure:

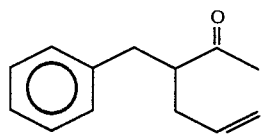

(Conditions: Field strength: 100 MHz; solvent: CFCl₃).

Bulked fractions 8-20 containing the compounds having the structures:

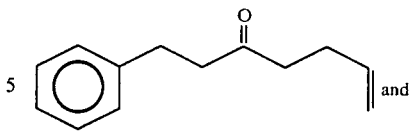

has a sweet, fruity, raspberry-like, jasmin, floral and rosey aroma with jasmin topnotes. The ratio of compounds having the structure:

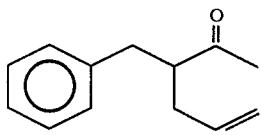

to the compound having the structure:

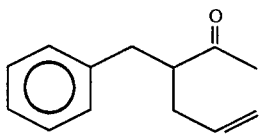

is 1:4.

EXAMPLE IX

PREPARATION OF MIXTURE OF 1-UNDECEN-5-ONE

AND 4-(1-PENTYL)-1-HEXEN-5-ONE

Reactions

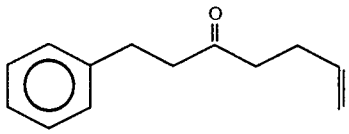

and

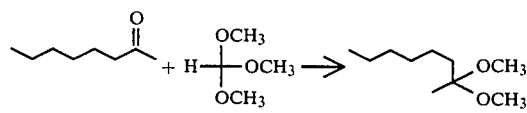

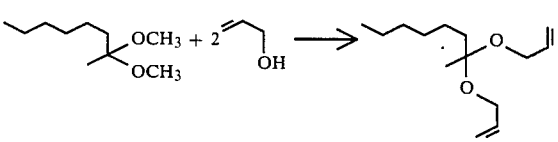

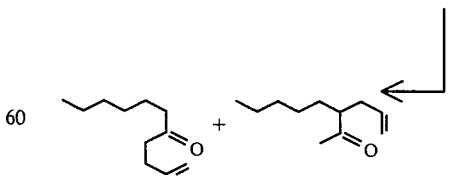

Into a 2 liter reaction flask equipped with stirrer, thermometer, reflux condenser, bidwell trap, and heating mantle is placed 624 grams of methyl hexyl ketone and 8 ml. concentrated hydrochloric acid. Over a period of 30 minutes 530 grams of trimethylorthoformate is added to the reaction mass. The reaction mass is then maintained with stirring at a temperature of 60° C. for a period of three hours. At the end of the three hour period, 10 grams of sodium carbonate is added to the reaction mass and, with stirring, 300 ml. water is added to the reaction mass. The organic phase is separated from the aqueous phase and the organic phase is placed in a 2 liter autoclave.

Also, 406 grams of allyl alcohol and 1 gram of citric acid is added to the autoclave. The autoclave is then sealed and heated to 150° C. under pressure and maintained at 150° C. under pressure for a period of two hours. At the end of the two hour period the autoclave is cooled, opened and the contents filtered. The contents are then distilled on a 12" Goodloe column yielding the following fractions:

| FRACTION NO. | VAPOR TEMP. (°C.) | LIQUID TEMP. (°C.) | VACUUM mm/Hg. PRESSURE |
|---|---|---|---|
| 1 | 28/45 | 50/68 | 8.0 |
| 2 | 55 | 70 | 8.0 |
| 3 | 30 | 52 | 1.6 |
| 4 | 30 | 55 | 1.6 |
| 5 | 30 | 55 | 3.0 |
| 6 | 35 | 52 | 1.8 |
| 7 | 30 | 52 | 1.6 |
| 8 | 30 | 52 | 1.6 |
| 9 | 38 | 63 | 4.0 |
| 10 | 45 | 70 | 6.0 |
| 11 | 45 | 73 | 6.0 |
| 12 | 45 | 78 | 6.0 |
| 13 | 48 | 80 | 6.0 |
| 14 | 62 | 80 | 6.0 |
| 15 | 76 | 86 | 6.0 |
| 16 | 75 | 85 | 6.0 |
| 17 | 75 | 85 | 6.0 |
| 18 | 75 | 85 | 6.0 |
| 19 | 75 | 85 | 6.0 |
| 20 | 75 | 85 | 6.0 |
| 21 | 75 | 87 | 6.0 |
| 22 | 75 | 112 | 6.0 |
| 23 | 60 | 230 | 6.0 |

FIG. 13 is the GLC profile for the crude reaction product (conditions: SE-30 column programmed at 160° C. isothermal). The peak indicated by Reference Numeral 130 is the peak for the compounds having the structures:

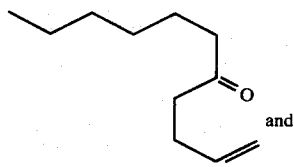

and

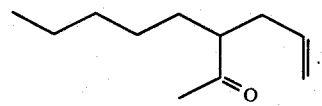

FIG. 14 is the NMR spectrum for fraction 10 of the foregoing distillation containing the compound having the structure:

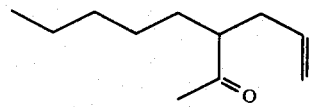

(Conditions: Solvent: CFCl₃; field strength: 100 MHz).

Bulked fractions 17–22 of the foregoing distillation has a licorice, aniseed aroma with fruity, pineapple, green, woody, herbaceous, minty and camphoraceous topnotes. The isomer ratio of bulked fractions 17–22 of the compound having the structure:

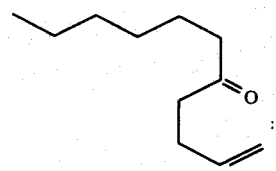

the compound having the structure:

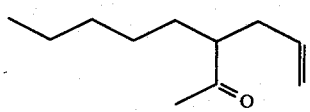

is 1:4.

EXAMPLE X(A)

PREPARATION OF ALLYL ALPHA IONONE ISOMER MIXTURE

Reactions

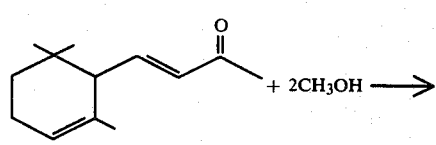

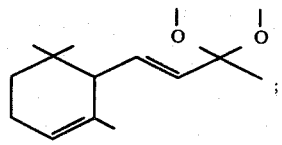

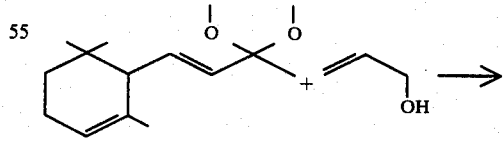

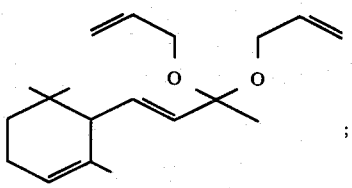

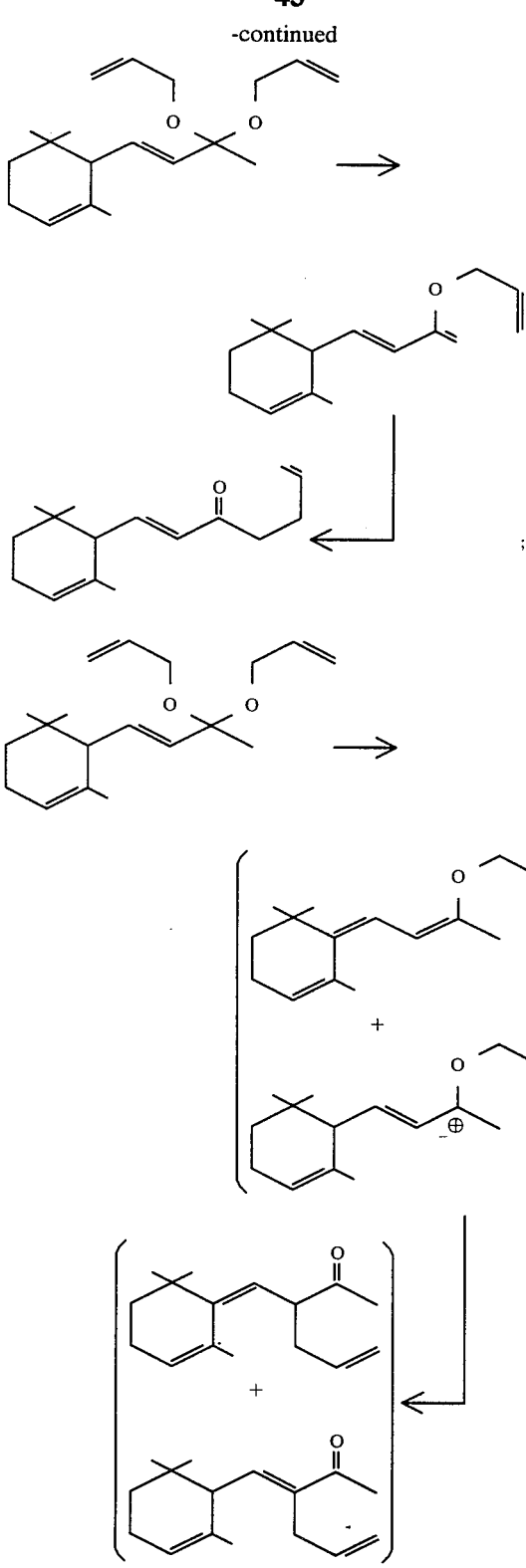

chloric acid is added to the reaction mass. The reaction mass is then aged at −10° C. for a period of 20 minutes. At the end of the 20 minute period the reaction mass is neutralized with solid anhydrous sodium acetate.

4.0 Grams of anhydrous citric acid followed by rapid addition of 870 grams of allyl alcohol (15.0 moles) is added to the reaction mass. The reaction mass is warmed to 25° C. The reaction mass is then heated gradually to 150° C. at atmospheric pressure. During this period, methylformate, methanol and allyl alcohol are distilled through the bidwell trap at, respectively, 55°-64° C., 64°-90° C. and 90°-150° C. After 7 hours the reaction mass reaches 150° C. The reaction mass is then stirred at 150° C. for a period of 2 hours. At the end of the 2 hour period, the reaction mass is cooled to 25° C. and washed with 1 liter of saturated sodium chloride solution. The washed crude reaction mass weighing 1825 grams is charged to a 3 liter still yielding the following fractions:

| FRACTION NO. | VAPOR TEMP. (°C.) | LIQUID TEMP. (°C.) | VACUUM mm/Hg. PRESSURE |
|---|---|---|---|
| 1 | 30-110 | 100-140 | 2.3 |
| 2 | 116 | 144 | 2.3 |
| 3 | 122 | 145 | 2.3 |
| 4 | 128 | 148 | 2.3 |
| 5 | 128 | 220 | 2.3 |

Fractions 2-5 from the first distillation is then distilled on an 18″×2″ Goodloe column yielding the following fractions:

| FRACTION NO. | VAPOR TEMP. (°C.) | LIQUID TEMP. (°C.) | VACUUM mm/Hg. PRESSURE |
|---|---|---|---|
| 1 | 80/83 | 138/138 | 2/1 |
| 2 | 92 | 138 | 3.0 |
| 3 | 87 | 138 | 1.0 |
| 4 | 90 | 140 | 1.0 |
| 5 | 100 | 140 | 1.0 |
| 6 | 109 | 144 | 1.0 |
| 7 | 109 | 145 | 1.0 |
| 8 | 109 | 148 | 1.0 |
| 9 | 109 | 149 | 1.0 |
| 10 | 109 | 149 | 1.0 |
| 11 | 111 | 149 | 1.0 |
| 12 | 111 | 150 | 1.0 |
| 13 | 111 | 150 | 1.0 |
| 14 | 111 | 180 | 1.0 |
| 15 | 111 | 200 | 1.0 |
| 16 | 110 | 220 | 1.0 |

Fractions 1-3 contain recovered alpha ionone. Fractions 7-15 are bulked and contain the isomers having the structures:

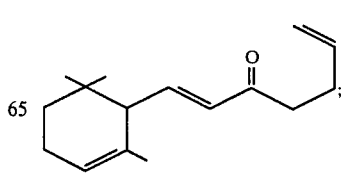

Into a 5 liter reaction flask equipped with stirrer, thermometer, addition funnel, bidwell trap, heating mantle, cooling bath and reflux condenser is placed 640 grams (20 moles) of methanol, 1520 grams (8.0 moles) of alpha ionone and 934 grams (8.8 moles) of trimethylorthoformate. The reaction flask is cooled to −10° C. and maintained at −10° C. to −20° C. Over a period of five minutes, 3.6 grams (0.36 moles) of concentrated hydro- -continued

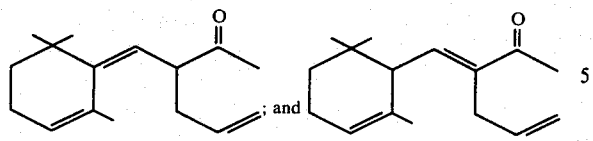

with the mole ratio of compound having the structure:

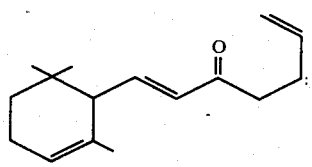

compounds having the structures:

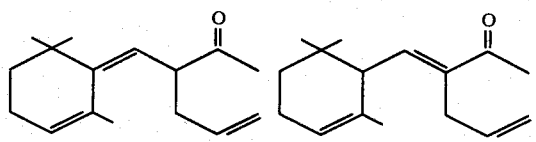

being about 48:1. This represents an exception to the rule that the branched rather than the straight chain material is produced via Claisen rearrangement using a citric acid catalyst.

The resulting product has a sweet, floral, fruity, barklike and green aroma profile.

FIG. 15 is the GLC profile for the crude reaction product prior to distillation (Conditions: SE-30 column programmed at 100°-220° C. at 8° C. per minute).

FIG. 16 is the GLC profile for bulked fractions 7-15 of the second distillation (Conditions: SE-30 column programmed at 100°-220° C. at 8° C. per minute).

EXAMPLE X(B)

PREPARATION OF ALLYL BETA IONONE ISOMER mixture

Reactions

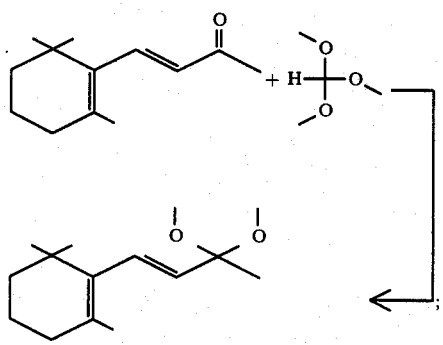

-continued

Into a 3 liter reaction vessel equipped with stirrer, thermometer, reflux condenser and cooling coils is placed 650 grams of beta ionone (3.4 moles); 700 ml. anhydrous methanol; and 394 grams (3.7 moles) of trimethylorthoformate. With stirring, the reaction mass is cooled to −10° C. Over a period of 30 minutes while maintaining the reaction mass at −10° C, 3 grams of concentrated hydrochloric acid is added to the reaction mass. After the addition of hydrochloric acid, at −10° C. over a period of 15 minutes, 3 grams of sodium acetate is added. After the addition of the sodium acetate, over a period of 15 minutes, 470 ml. of allyl alcohol and 3.3 grams of citric acid is added to the reaction mass. The reaction mass is then heated and methylformate, methanol and allyl alcohol is removed via a bidwell trap. The reaction mass is maintained at 58° C. for a period of 4.5 hours while removing the above-mentioned products. The reaction mass is then heated to 140°-150° C. and maintained at 140°-150° C. with stirring for a period of 4 hours. At the end of the 4 hour period, the reaction mass is cooled to room temperature and is washed with one 500 ml. portion of saturated sodium chloride solution.

The reaction mass is then distilled on a 2" splash column yielding the following fractions:

| FRACTION NO. | VAPOR TEMP. (°C.) | LIQUID TEMP. (°C.) | VACUUM mm/Hg. PRESSURE |
|---|---|---|---|
| 1 | 84/105 | 110/118 | 2.8/2.5 |
| 2 | 105 | 127 | 2.5 |
| 3 | 120 | 140 | 2.5 |
| 4 | 128 | 200 | 2.5 |

Fractions 2–4 are bulked and redistilled on a 1' Goodloe column yielding the following fractions:

| FRACTION NO. | VAPOR TEMP. (°C.) | LIQUID TEMP. (°C.) | VACUUM mm/Hg. PRESSURE | REFLUX RATIO |
|---|---|---|---|---|
| 1 | 90 | 128 | 2.0 | 4:1 |
| 2 | 105 | 137 | 2.0 | 4:1 |
| 3 | 109 | 140 | 2.0 | 4:1 |
| 4 | 109 | 140 | 2.0 | 4:1 |
| 5 | 109 | 140 | 2.0 | 9:1 |
| 6 | 109 | 140 | 2.5 | 19:1 |
| 7 | 112 | 141 | 2.0 | 19:1 |
| 8 | 113 | 142 | 2.0 | 19:1 |
| 9 | 113 | 143 | 2.0 | 19:1 |
| 10 | 113 | 143 | 2.0 | 19:1 |
| 11 | 113 | 144 | 2.0 | 19:1 |
| 12 | 113 | 145 | 2.0 | 19:1 |
| 13 | 113 | 145 | 2.0 | 19:1 |
| 14 | 118 | 155 | 2.0 | 19:1 |
| 15 | 118 | 147 | 2.0 | 19:1 |
| 16 | 120 | 147 | 2.0 | 19:1 |
| 17 | 121 | 147 | 2.0 | 19:1 |
| 18 | 126 | 150 | 2.0 | 19:1 |
| 19 | 128 | 158 | 2.0 | 19:1 |
| 20 | 132 | 195 | 2.0 | 19:1 |
| 21 | 125 | 220 | 2.0 | 19:1 |

FIG. 17 is the GLC profile for the crude reaction product prior to distillation on a 2" splash column, containing the compounds having the structures:

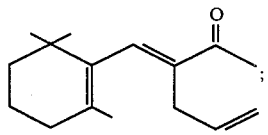

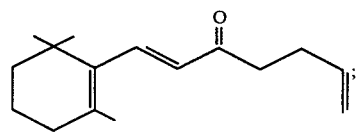

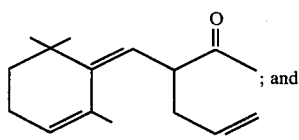
; and

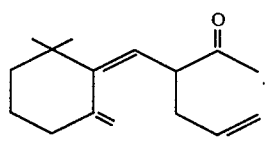

FIG. 18 is the GLC profile for fraction 14 of the foregoing second distillation on the 1' Goodloe column containing the compounds having the structures:

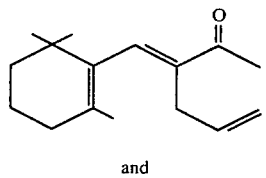

and

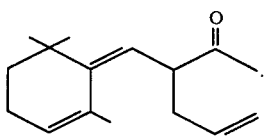

The resulting mixture has a floral, fruity and green aroma profile.

EXAMPLE XI

SPICY-FLORAL FRAGRANCES

The following spicy-floral fragrances are prepared:

| INGREDIENTS | XI (A) | XI (B) | XI (C) | XI (D) | XI (E) | XI (F) |
|---|---|---|---|---|---|---|
| Coumarin | 6.0 | 6.0 | 6.0 | 6.0 | 6.0 | 6.0 |
| Musk Ambrette | 8.0 | 8.0 | 8.0 | 8.0 | 8.0 | 8.0 |
| Benzyl Salicylate | 12.0 | 12.0 | 12.0 | 12.0 | 12.0 | 12.0 |
| Bergamot Oil | 6.0 | 6.0 | 6.0 | 6.0 | 6.0 | 6.0 |
| Hydroxycitronellal | 5.0 | 5.0 | 5.0 | 5.0 | 5.0 | 5.0 |
| Lavender Oil | 4.0 | 4.0 | 4.0 | 4.0 | 4.0 | 4.0 |
| Patchouli Oil Light | 1.0 | 1.0 | 1.0 | 1.0 | 1.0 | 1.0 |
| Phenyl Ethyl Alcohol | 6.0 | 6.0 | 6.0 | 6.0 | 6.0 | 6.0 |
| Gamma Methyl Ionone | 1.0 | 1.0 | 1.0 | 1.0 | 1.0 | 1.0 |
| Vetivert Oil | 8.0 | 8.0 | 8.0 | 8.0 | 8.0 | 8.0 |
| Benzyl Acetate | 14.0 | 14.0 | 14.0 | 14.0 | 14.0 | 14.0 |
| Linalool | 8.0 | 8.0 | 8.0 | 8.0 | 8.0 | 8.0 |
| Amyl Cinnamic Aldehyde | 10.0 | 10.0 | 10.0 | 10.0 | 10.0 | 10.0 |
| Indole (10% in diethyl phthalate) | 1.0 | 1.0 | 1.0 | 1.0 | 1.0 | 1.0 |
| Eugenol | 2.0 | 2.0 | 2.0 | 2.0 | 2.0 | 2.0 |
| Mixture of compounds having the structures: 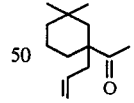 and 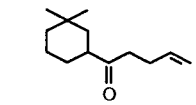 produced according to Example III (mole ratio of compound having the structure: 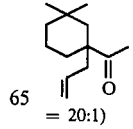 to compound having the structure: 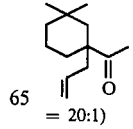 = 20:1) | 8.0 | 0.0 | 0.0 | 0.0 | 0.0 | 0.0 |
| Mixture of compounds having the structures: | 0.0 | 8.0 | 0.0 | 0.0 | 0.0 | 0.0 |

| INGREDIENTS | XI (A) | XI (B) | XI (C) | XI (D) | XI (E) | XI (F) |
|---|---|---|---|---|---|---|
| 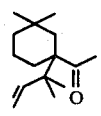 and 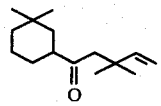 with the mole ratio of compound having the structure: 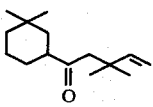 to the compound having the structure:  being 1:4 | | | | | | |
| The dimethyl ketal of 1-acetyl-3,3-dimethyl cyclohexane produced according to Example I | 0.0 | 0.0 | 8.0 | 0.0 | 0.0 | 0.0 |
| Mixture of compounds having the structures: 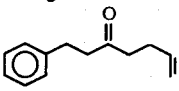 and 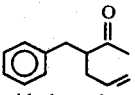 with the mole ratio of compound having the structure: 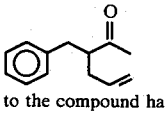 to the compound having the structure: 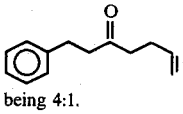 being 4:1. | 0.0 | 0.0 | 0.0 | 8.0 | 0.0 | 0.0 |
| Mixture of compounds having the structures: 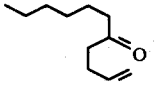 and 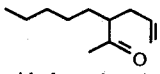 with the mole ratio of compound having the structure: 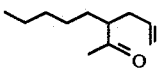 to the compound having the structure: 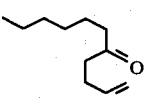 being 4:1. | 0.0 | 0.0 | 0.0 | 0.0 | 8.0 | 0.0 |
| Mixture of compounds having the structures: 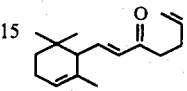 and 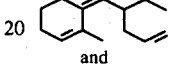 produced according to Example X (A) with the mole ratio of compound having the structure: 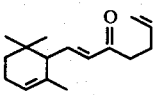 to the compounds having the structures: 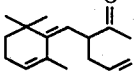 and 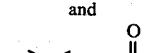 being 46:1. | 0.0 | 0.0 | 0.0 | 0.0 | 0.0 | 8.0 |

The perfume formulations can be described as follows:

Example XI(A): Spicy and floral with galbanum-like, green herbaceous and chypre undertones.

Example XI(B): Spicy and floral with woody, pine and floral undertones and citrusy and lemony topnotes.

Example XI(C): Spicy and floral with a pear undertone and green, cedarwood and minty topnotes.

Example XI(D): Spicy and floral with sweet, fruity, raspberry, jasmin, floral and rosey undertones and jasmin topnotes.

Example XI(E): Spicy and floral with licorice, aniseed undertones and fruity, pineapple, green, woody, herbaceous, minty and camphoraceous topnotes.

Example XI(F): Spicy and floral aroma with sweet, floral, fruity, bark-like and green undertones.

EXAMPLE XII

PREPARATION OF A COSMETIC POWDER COMPOSITION

A cosmetic powder is prepared by mixing in a ball mill 100 grams of talcum powder with 0.25 grams of a perfume substance as set forth in Table III below. The resulting powder has an excellent aroma as set forth in Table III below:

TABLE III

| PERFUME SUBSTANCE | AROMA DESCRIPTION |
|---|---|
| Mixture of compounds having the the structure: 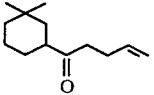 and  prepared according to Example III with the mole ratio of compound having the structure: 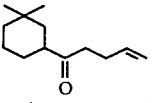 to the compound having the structure: 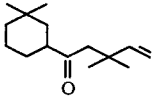 being 20:1 | A galbanum-like, floral, green, herbaceous and chypre aroma profile. |
| Mixture of compounds having the structures:  and 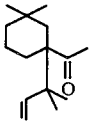 with the mole ratio of compound having the structure: 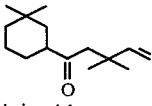 to the compound having the structure: 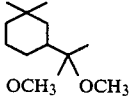 being 4:1. | A woody, piney, floral aroma with citrusy lemony topnotes. |
| Compound having the structure: 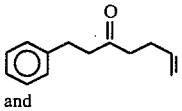 prepared according to Example I. | A sweet, pear, fruity aroma with green, cedarwood and minty topnotes. |
| Mixture of compounds having the structures: 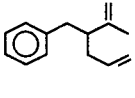 and 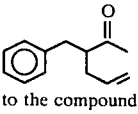 with the mole ratio of compound having the structure: 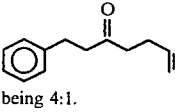 to the compound having the structure: 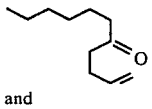 being 4:1. | A sweet, fruity, raspberry-like, jasmin, floral and rosey aroma with jasmin topnotes. |
| Mixture of compounds having the structures: 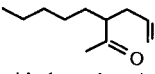 and 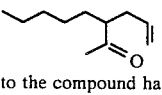 with the mole ratio of compound having the structure: 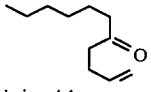 to the compound having the structure: 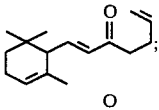 being 4:1 | A licorice and aniseed aroma with fruity, pineapple, green, woody, herbaceous, minty and camphoraceous topnotes. |
| Mixture of compounds having the structures: 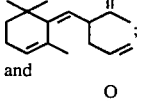 and 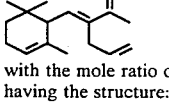 with the mole ratio of compound having the structure: 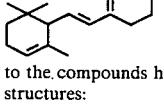 to the compounds having the structures: 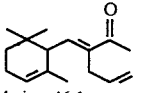 being 46:1. | A sweet, floral, fruity, bark-like and green aroma profile. |
| Perfume composition of Example XI(A) | Spicy and floral with galbanum-like, green, herbaceous and chypre undertones. |
| Perfume composition of Example XI(B) | Spicy and floral with woody, pine and floral undertones and citrusy and lemony topnotes. |

TABLE III-continued

| PERFUME SUBSTANCE | AROMA DESCRIPTION |
|---|---|
| Perfume composition of Example XI(C) | Spicy and floral with a pear undertone and green, cedarwood and minty topnotes. |
| Perfume composition of Example XI(D) | Spicy and floral with sweet, fruity, raspberry, jasmin, floral and rosey undertones and jasmin topnotes. |
| Perfume composition of Example XI(E) | Spicy and floral with licorice, aniseed undertones and fruity, pineapple, green, woody, herbaceous, minty and camphoraceous topnotes. |
| Perfume composition of Example XI(F) | Spicy and floral aroma with sweet, floral, fruity, bark-like and green undertones. |

EXAMPLE XIII

PERFUME LIQUID DETERGENT

Concentrated liquid detergent (lysine salt of n-dodecylbenzene sulfonic acid as more specifically described in U.S. Pat. No. 3,948,818, issued on Apr. 6, 1976, the specification for which is incorporated herein by reference) with aroma nuances as set forth in Table III of Example XII, supra, are prepared containing 0.10%, 0.15%, 0.20%, 0.25%, 0.30% and 0.35% of the substances as set forth in Table III of Example XII, supra. They are prepared by adding and homogeneously mixing the appropriate quantity of fragrance formulation of Table III of Example XII, supra, in the liquid detergents. The detergents all possess excellent aromas, the intensity increasing with greater concentration of perfume substance of Table III of Example XII.

EXAMPLE XIV

PREPARATION OF A COLOGNE AND HANDKERCHIEF PERFUME

The perfume substances as set forth in Table III of Example XII, supra, are incorporated into colognes at concentrations of 2.0%, 2.5%, 3.0%, 3.5%, 4.0%, 4.5% and 5.0% in 75%, 80%, 85% and 90% aqueous food grade ethanol; and into handkerchief perfumes at concentrations of 15%, 20%, 25%, and 30% (in 80%, 85%, 90% and 95% aqueous food grade ethanol solutions). Distinctive and definitive aroma nuances as set forth in Table III of Example XII are imparted to the colognes and to the handerchief perfumes at all levels indicated above.

EXAMPLE XV

PREPARATION OF SOAP COMPOSITIONS

One hundred grams of soap chips (IVORY®, produced by the Procter & Gamble Company of Cincinnati, Ohio are mixed with 1 gram of each of the perfumery substances of Table III of Example XII, supra, until homogeneous compositions are obtained. In each of the cases, the homogeneous compositions are heated under 3 atmospheres pressure at 180° C. for a period of three hours and the resulting liquids are placed into soap molds. The resulting soap cakes, on cooling, manifest excellent aromas as set forth in Table III of Example XII, supra.

EXAMPLE XVI

PREPARATION OF SOLID DETERGENT COMPOSITIONS

A detergent is prepared from the following ingredients according to Example I of Canadian Pat. No. 1,007,948, (the specification for which is incorporated herein by reference):

| Ingredient | Percent by Weight |
|---|---|
| Neodol ® 45-11 (a $C_{14}$-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is phosphate-free detergent. A total of 100 grams of said detergent is admixed with 0.10, 0.15, 0.20 and 0.25 grams of the substances of Table III of Example XII, supra. The detergent samples in each case have excellent aromas as set forth in Table III of Example XII, supra.

EXAMPLE XVII

Utilizing the procedure of Example I at column 15 of U.S. Pat. No. 3,632,396, (the disclosure of which is incorporated by reference herein) a nonwoven cloth substrate useful as a drier-added fabric softening article of manufacture is prepared wherein the substrate, the substrate coating and the outer coating and the perfuming material are as follows:
1. A water dissolvable paper ("Dissolvo Paper");
2. Adogen 448 (melting point about 140° F.) as the substrate coating; and
3. An outer coating having the following formulation (melting point about 150° F.):
   57% $C_{20-22}$ HAPS
   22% isopropyl alcohol
   20% antistatic agent
   1 of one of the perfume substances of Table III of Example XII, supra.

Fabric softening compositions having aromas as set forth in Table III of Example XII are prepared which essentially consist of a substrate having a weight of about 3 grams per 100 square inches; a substrate coating having a weight of about 1.85 grams per 100 grams of substrate; and an outer coating having a weight of about 1.4 grams per 100 square inches of substrate, thereby providing a total aromatized substrate and outer coating weight ratio of about 1:1 by weight of the substrate. The aromas as set forth in Table III of Example XII are imparted in a pleasant manner to the head space in the drier on operation thereof using each of the drier-added fabric softening nonwoven fabric samples.

In the following examples, Aromox ® DMC-W and Aromox ® DMMC-W are 30% aqueous solutions of dimethyl cocoamine oxide; and Aromox ® NCMDW is a 40% aqueous solution of N-cocomorpholine oxide produced by Armac Division of ADZO of Chicago, Ill.

EXAMPLE XVIII

Four drops of one or more of the perfume substances as set forth in Table III of Example XII, supra, is added to 2 grams of Aromox ® DMC-W to produce a clear premix. The clear premix is added to 200 grams of CLOROX ® with stirring resulting in a clear, stable, single phase solution. Sufficient 1M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" odor but does have a faint, pleasant aroma as set forth in Table III of Example XII, supra. Furthermore, no such characteristic "hypochlorite" aroma is retained on the hands of the individual handling such laundry in both the wet and the dry states.

EXAMPLE XIX

Aromox ® DMMC-W in various quantities is mixed with 0.1 grams of each of the substances of Table III of Example XII, supra. The resulting premixes are then added to 200 grams of an aqueous 5% sodium hypochlorite solution. Sufficient 12.5M aqueous NaOH is added to bring the pH of each of the mixtures up to 13. The following results are obtained:

| Percentage Aromox ® DMMC-W | Clarity of hypochlorite solution after addition of premix |
|---|---|
| 0.23% | Clear after three days |
| 0.15% | Clear after three days |
| 0.08% | Initially slightly turbid; two phases exist after three days |

When the 5% aqueous sodium hypochlorite solutions are used as laundry bleaches, the resulting laundry batches on dry-out in an atmosphere of 65% relative humidity yields substantially no characteristic "hypochlorite" odor but do have faint, pleasant aromas as set forth in Table III of Example XII, supra. Furthermore, no such characteristic "hypochlorite" aroma is retained on the hands of the individual handling such laundry batches in both the wet and dry states.

EXAMPLE XX

Two grams of Aromox ® DMMC-W are admixed with eight drops of each of the perfume substances of Table III of Example XII, supra. Each of the premixes is then added with stirring to 200 grams of a 7% aqueous solution of lithium hypochlorite. Sufficient 3M aqueous LiOH is added to bring the pH of the solution to 13.4. The mixtures are then heated to 120° F. and maintained at that temperature with stirring for a period of one week. The resulting solution remains clear in a single phase. When used as laundry bleaches, the resulting bleached laundry batches on dry-out in an atmosphere of 50% relative humidity retain an aroma as described in Table III of Example XII whereas without the use of the substances of Table III of Example XII, the bleached laundry batches have faint characteristic disagreeable "hypochlorite" aromas.

EXAMPLE XXI

Two grams of Aromox ® DMMC-W are admixed with eight drops of each of the substances of Table III of Example XII, supra. The premixes are then added with stirring to 200 grams of a mixture containing 4.5% aqueous sodium hypochlorite and 4.5% aqueous lithium hypochlorite. Sufficient 4M aqueous LiOH is added to bring the pH of the solutions to 13.4. The mixtures are then heated to 120° F. and maintained at that temperature for a period of one week. The resulting solutions remain clear in a single phase. When used as laundry bleach, the resulting bleached laundry batches on dry-out in an atmosphere of 50% relative humidity retain an aroma as set forth in Table III of Example XII, supra, whereas without the use of the perfume substances as set forth in Table III of Example XII, supra, the bleached laundry batches have faint characteristic and disagreeable "hypochlorite" aromas.

EXAMPLE XXII

Two grams of Aromox ® DMMC-W are admixed with eight drops of one of the perfume substances of Table III of Example XII, supra. These premixes are then added with stirring to 200 grams of mixture containing 4% aqueous sodium hypochlorite and 4% aqueous lithium hypochlorite. Sufficient 2M aqueous NaOH is added to bring the pH of the solutions to 13.4. The mixtures are then heated to 110° F. and maintained at that temperature with stirring for a period of two weeks. The resulting solutions remain clear as a single phase when used as laundry bleaches. The resulting bleached laundry batches on dry-out in an atmosphere of 50% relative humidity retain aromas as set forth in Table III of Example XII, supra whereas without the use of the perfume substances of Table III of Example XII, supra, the bleached laundry batches have faint, characteristic disagreeable "hypochlorite" aromas.

EXAMPLE XXIII

Four drops of each of the substances of Table III of Example XIII, supra, are added to 1.5 grams of Aromox ® NCMDW to produce a clear premix. The clear premixes are added to 200 grams in each case of CLOROX ® with stirring resulting in a clear single phase solution. Sufficient 1M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic hypochlorite aroma but does have a faint pleasant aroma as set forth in Table III of Example XII, supra. Furthermore, no such characteristic "hypochlorite" aroma is retained on the hands of the individual handling such laundry in both the wet and the dry states.

EXAMPLE XXIV

Four drops of each of the substances of Table III of Example XII, supra, are added to 1 gram of n-undecyl dimethyl amine oxide to produce a clear premix in each case. The clear premix is added to 200 grams of CLOROX ® with stirring resulting in a clear, single phase solution. Sufficient 1M aqueous NaOH is added to bring the pH of the mixture to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic hypochlorite odor but does have a faint pleasant odor as set forth in Table III of Example XII, supra. Furthermore, no such characteristic "hypochlorite" odor is retained on the hands of the individual handling such laundry in both the wet and the dry states.

EXAMPLE XXV

Four drops of each of the substances of Table III of Example XII, supra, is added to 1 gram of n-dodecyl dimethyl amine oxide to produce a clear premix. The clear premix is added to 200 grams of CLOROX® with stirring resulting in a clear stable single phase solution. Sufficient 1M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dryout in an atmosphere of 65% relative humidity yields substantially no characteristic "hypochlorite" odor but does have a faint pleasant aroma as set forth in Table III of Example XII, supra. Furthermore, no such characteristic "hypochlorite" aroma is retained on the hands of the individual handling such laundry in both the wet and the dry states.

EXAMPLE XXVI

One gram of n-tridecyl dimethyl amine oxide is admixed with eight drops of each of the substances of Table III of Example XII, supra. Each of the premixes is then, with stirring, added to 200 grams of a 7% aqueous solution of lithium hypochlorite. Sufficient 3M aqueous LiOH is added to bring the pH of the solution to 13.4. The mixture is then heated to 120° F. and maintained at that temperature with stirring for a period of one week. The resulting solution remains clear in a single phase. When used as a laundry bleach, the resulting bleached laundry on dryout in an atmosphere of 50% relative humidity retains an aroma as set forth in Table III of Example XII, supra; whereas without the use of any of the substances of Table III of Example XII, supra, the bleached laundry has faint, chrarcteristic, disagreeable "hypochlorite" aroma.

What is claimed is:

1. A ketone-containing product prepared according to the process comprising the steps of (1) reacting at a temperature in the range of from about −10° C. up to about 50° C. trimethyl orthoformate with β-ionone according to the reaction:

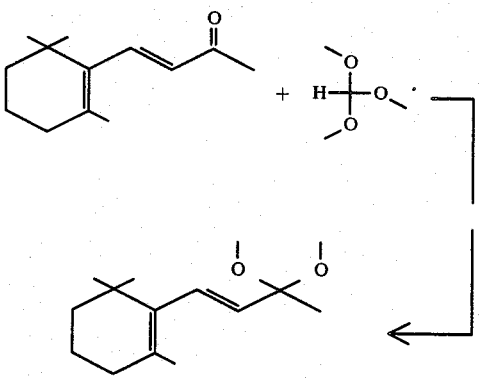

to form a ketal-containing composition with the mole ratio of β-ionone:trimethyl orthoformate being from about 1:1 to about 1:2; (ii) then reacting the ketal-containing composition with allyl alcohol at a temperature in the range of from about 120° C. up to about 220° C. according to the reaction:

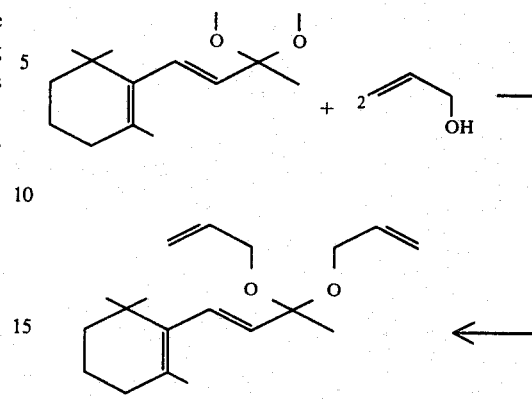

in order to form a diallyl ketal with the mole ratio of ketal-containing composition:allyl alcohol varying from about 1:1 up to about 1:3; then rearranging the resulting diallyl ketal at a temperature of from about 120° C. up to about 220° C. according to the reaction:

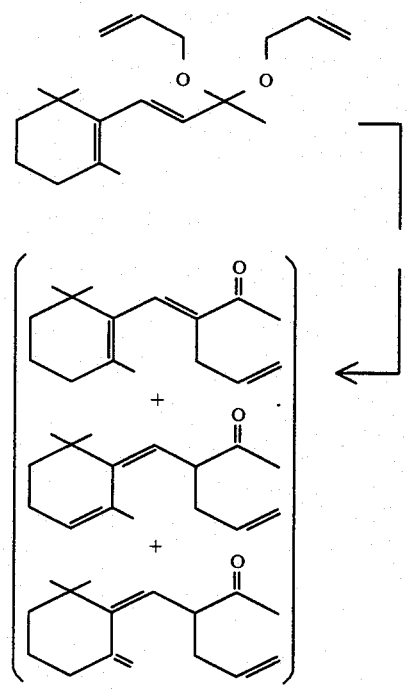

at a pH of between 2 and 6.5 in the presence of a citric acid catalyst and then fractionally distilling the resulting product at a vapor temperature of 105°-128° C. at 2.5 mm/Hg pressure.

2. A process for augmenting or enhancing the aroma of a consumable material selected from the group consisting of perfume compositions, perfumed articles and colognes comprising the step of adding to said consumable material an aroma augmenting or enhancing quantity of the product defined according to claim 1.

3. The product of claim 1 wherein in the process, the rearrangement reaction:

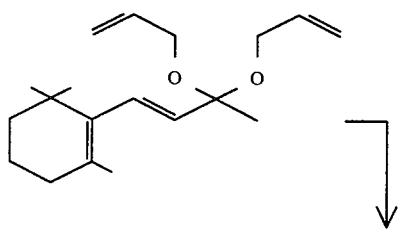
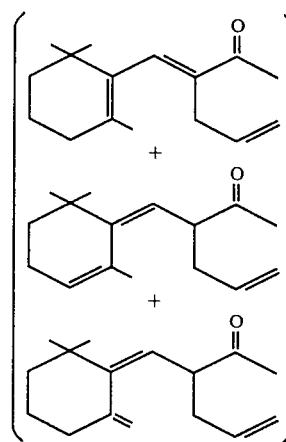
is carried out at 150° C.
4. A process for augmenting or enhancing the aroma of a consumable material selected from the group consisting of perfume compositions, perfumed articles and colognes comprising the step of adding to said consumable material, an aroma augmenting or enhancing quanitity of the product defined according to claim 3.
* * * * *